(12) United States Patent
Hasegawa et al.

(10) Patent No.: US 10,005,181 B2
(45) Date of Patent: Jun. 26, 2018

(54) MANIPULATOR INITIALIZATION METHOD, MANIPULATOR, AND MANIPULATOR SYSTEM

(71) Applicant: OLYMPUS CORPORATION, Tokyo (JP)

(72) Inventors: Mitsuaki Hasegawa, Tokyo (JP); Toshihiro Yoshii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 59 days.

(21) Appl. No.: 15/236,623

(22) Filed: Aug. 15, 2016

(65) Prior Publication Data

US 2016/0346924 A1    Dec. 1, 2016

Related U.S. Application Data

(63) Continuation of application No. PCT/JP2015/054759, filed on Feb. 20, 2015.

(30) Foreign Application Priority Data

Feb. 21, 2014   (JP) .................................. 2014-032248

(51) Int. Cl.
  *B25J 9/16*   (2006.01)
  *A61B 34/30*   (2016.01)
  *A61B 34/00*   (2016.01)
(52) U.S. Cl.
  CPC .............. *B25J 9/1612* (2013.01); *A61B 34/30* (2016.02); *A61B 34/71* (2016.02);
  (Continued)
(58) Field of Classification Search
  CPC ........ B25J 9/1612; A61B 34/30; A61B 34/71; A61B 2034/301; A61B 2034/715; G05B 2219/45118
  (Continued)

(56) References Cited

U.S. PATENT DOCUMENTS

2004/0092912 A1* 5/2004 Jinno ............... A61B 17/00234
  606/1
2004/0193015 A1* 9/2004 Ikeda ................. A61B 1/00039
  600/146
(Continued)

FOREIGN PATENT DOCUMENTS

EP     2 108 329 A2   10/2009
JP     H08-299364 A   11/1996
(Continued)

OTHER PUBLICATIONS

Extended Supplementary European Search Report dated Oct. 4, 2017 in European Patent Application No. 15 75 1615 4.
(Continued)

*Primary Examiner* — Jaime Figueroa
(74) *Attorney, Agent, or Firm* — Scully, Scott, Murphy & Presser, P.C.

(57) ABSTRACT

An initialization method for a manipulator includes: a reference angle maintaining step of setting a rotational angle of a joint part to a reference angle that has been predetermined, and maintaining the reference angle in a state where a driving force relay part is switched to a driving force release state; a drive part coupling step of switching the driving force relay part to a driving force relay state in a state where the joint part is arranged at a position where an initialization operation is performed after the reference angle maintaining step is performed; and an origin setting step of performing matching of a drive origin of a drive part according to a state of the rotational angle.

15 Claims, 20 Drawing Sheets

(52) U.S. Cl.
 CPC ... *A61B 2034/301* (2016.02); *A61B 2034/715* (2016.02); *G05B 2219/45118* (2013.01)

(58) Field of Classification Search
 USPC .......................................................... 700/245
 See application file for complete search history.

(56) References Cited

U.S. PATENT DOCUMENTS

| | | |
|---|---|---|
| 2004/0199147 A1 | 10/2004 | Nishizawa et al. |
| 2007/0013336 A1* | 1/2007 | Nowlin .................. B25J 9/1682 318/568.21 |
| 2008/0046122 A1* | 2/2008 | Manzo ............... A61B 1/00149 700/245 |
| 2008/0103491 A1* | 5/2008 | Omori .................... A61B 17/29 606/1 |
| 2009/0012365 A1 | 1/2009 | Ueno et al. |
| 2009/0105726 A1* | 4/2009 | Sugiyama .......... A61B 18/1492 606/130 |
| 2009/0112060 A1* | 4/2009 | Sugiyama .......... A61B 1/00098 600/104 |
| 2009/0253959 A1* | 10/2009 | Yoshie ............... A61B 1/00133 600/114 |
| 2009/0259340 A1* | 10/2009 | Umemoto ............ A61B 1/0051 700/275 |
| 2009/0326318 A1* | 12/2009 | Tognaccini ........ A61B 1/00183 600/104 |
| 2009/0326553 A1 | 12/2009 | Mustufa et al. |
| 2010/0082041 A1* | 4/2010 | Prisco .................... B25J 9/1045 606/130 |
| 2010/0168919 A1* | 7/2010 | Okamoto ................... B25J 9/06 700/275 |
| 2013/0184873 A1 | 7/2013 | Namiki |
| 2015/0127019 A1 | 5/2015 | Komuro et al. |

FOREIGN PATENT DOCUMENTS

| | | |
|---|---|---|
| JP | H10-174686 A | 6/1998 |
| JP | 2004-122286 A | 4/2004 |
| JP | 2007-029167 A | 2/2007 |
| JP | 2008-104854 A | 5/2008 |
| JP | 2009-101077 A | 5/2009 |
| JP | 2009-539573 A | 11/2009 |
| JP | 2012-504016 A | 2/2012 |
| JP | 2013-103074 A | 5/2013 |
| JP | 2014-012212 A | 1/2014 |
| WO | 2007/146987 A2 | 12/2007 |
| WO | 2010/039387 A1 | 4/2010 |
| WO | 2013/058405 A1 | 4/2013 |
| WO | WO 2013/073713 A1 | 5/2013 |
| WO | 2014/021222 A1 | 2/2014 |

OTHER PUBLICATIONS

International Search Report dated May 26, 2015 issued in PCT/JP2015/054759.

* cited by examiner

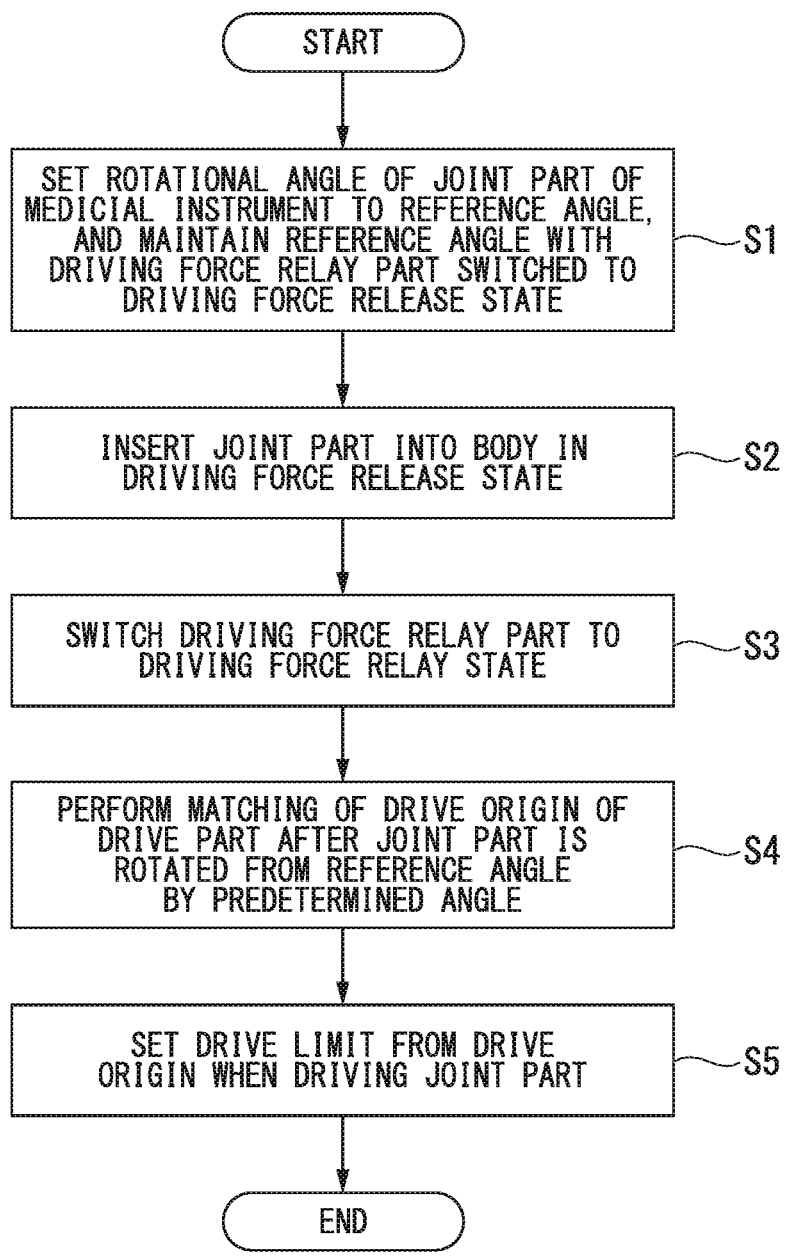

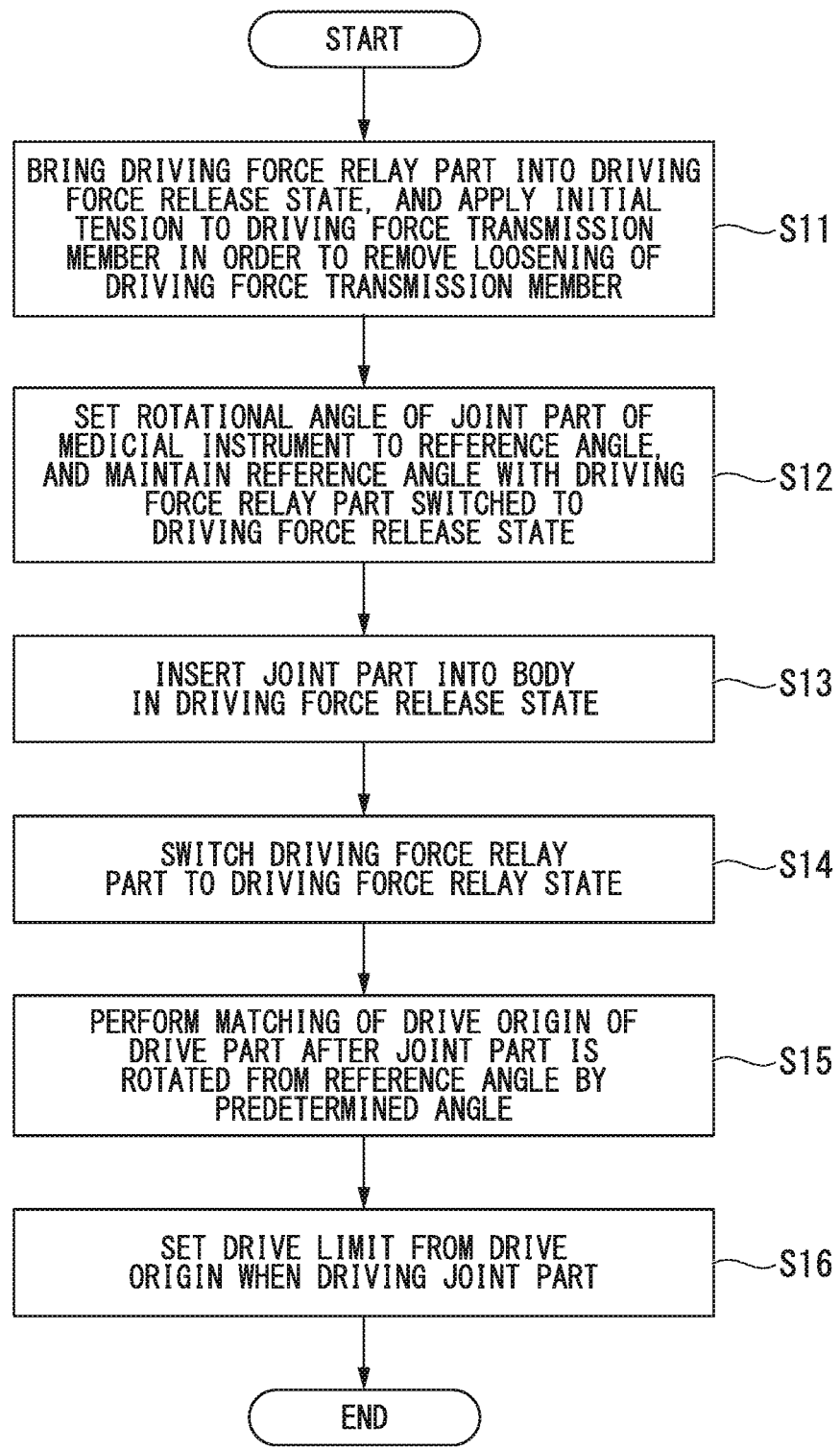

MANIPULATOR INITIALIZATION METHOD, MANIPULATOR, AND MANIPULATOR SYSTEM

CROSS REFERENCE TO RELATED APPLICATIONS

This application is a continuation application based on a PCT International Application No. PCT/JP2015/054759, filed on Feb. 20, 2015, whose priority is claimed on Japanese Patent Application No. 2014-032248, filed Feb. 21, 2014. Both of the contents of the PCT International Application and the Japanese Application are incorporated herein by reference.

BACKGROUND OF THE INVENTION

Field of the Invention

The present invention relates to a manipulator initialization method, a manipulator, and a manipulator system.

Description of Related Art

In the related art, from the viewpoint of reducing stress of a patient, a treatment tool is inserted into a channel of an endoscope, or a multi joint arm having the treatment tool at a distal end part of the endoscope is provided, the treatment tool is inserted into a body from a small hole made in a patient's abdomen or the like, and various kinds of treatment are performed under endoscope observation.

For example, Japanese Unexamined Patent Application, First Publication No. 2008-104854 describes a manipulator including an operation command part that is grasped and operated by a human's hand, and a working part that is detachably provided at the operation command part and has a grasper movably held by a distal end of a rigid shaft via a joint.

The operation command part is provided with an actuator block having a drive motor, and pulleys of the actuator block and the working part are detachably coupled together via an alignment pin.

A locking plate that sets the position of each pulley to an origin position of the working part is capable of being mounted on each pulley.

In order to perform treatment with such a manipulator, the working part is set to the origin position, for example, to a state where a movable part is extended in a straight state, by mounting the locking plate on the pulley of the working part from which the operation command part is detached. In the actuator block, the drive motor is set to the origin position of the motor. Then, the locking plate is removed from the working part, and the actuator block is mounted. Accordingly, in the manipulator, initialization is performed in a state where the origin position of the drive motor and the origin position of the working part coincide with each other. Therefore, the operation of starting driving from the origin position of the working part can be performed according to the operation of the operation command part.

SUMMARY OF THE INVENTION

According to a first aspect of the invention, an initialization method for a manipulator is provided, the manipulator including a medical instrument having a joint part that rotates an object to be rotated, a driving force transmission part that transmits a driving force to the joint part, a drive part that supplies the driving force to the driving force transmission part, and a driving force relay part capable of being switched between a driving force relay state where the driving force is relayed and a driving force release state where the driving force is cut off. The initialization method includes a reference angle maintaining step of setting the rotational angle of the joint part to a predetermined reference angle, and maintaining the reference angle in a state where the driving force relay part is switched to the driving force release state; a drive part coupling step of switching the driving force relay part to the driving force relay state in a state where the joint part is arranged at a position where an initialization operation is performed after the reference angle maintaining step is performed; and an origin setting step of performing matching of the drive origin of the drive part according to the state of the rotational angle.

According to the initialization method of a second aspect of the invention based on the above first aspect, the reference angle may have the rotational angle of the joint part as a rotatable limit angle.

According to the initialization method of a third aspect of the invention based on the above first or second aspect, the initialization method further includes: a rotational angle adjusting step of rotating the joint part to a predetermined angle from the reference angle performed before the origin setting step is performed.

According to the initialization method of a fourth aspect of the invention based on any one aspect of the above first to third aspects, the initialization method further includes: a drive limit setting step of setting a drive limit from the drive origin when the joint part is driven performed with respect to the drive part after the origin setting step is performed.

According to the initialization method of a fifth aspect of the invention based on any one aspect of the above first to fourth aspects, the driving force transmission part may include a linear driving force transmission member, and the initialization method further includes: an initial tension applying step of applying an initial tension to the driving force transmission member in order to remove loosening of the driving force transmission member may be performed before the origin setting step is performed.

According to the initialization method of a sixth aspect of the invention based on any one aspect of the above first to fifth aspects, the joint part may include a bending joint, and, in the reference angle maintaining step, the reference angle of the joint part including the bending joint may be set to a rotational angle that allows the operation of folding the object to be rotated coupled to the joint part.

According to a seventh aspect of the invention, a manipulator is provided including a medical instrument having a joint part that rotates an object to be rotated; a driving force transmission part that transmits a driving force to the joint part; a drive part that supplies the driving force to the driving force transmission part; a driving force relay part capable of being switched between a driving force relay state where the driving force is relayed and a driving force release state where the driving force is cut off; a reference angle maintaining part that sets the rotational angle of the joint part to a predetermined reference angle, and maintains the reference angle in a state where the driving force relay part is switched to the driving force release state; and a driving control unit that performs matching of the drive origin of the drive part according to the state of the rotational angle.

According to the manipulator of an eighth aspect of the invention based on the above seventh aspect, the reference angle may have the rotational angle of the joint part as a rotatable limit angle.

According to the manipulator of a ninth aspect of the invention based on the above seventh or eighth aspect, the driving control unit may perform the rotational angle adjustment of rotating the joint part to a predetermined angle from the reference angle before the matching of the driving origin of the drive part is performed.

According to the manipulator of a tenth aspect of the invention based on any one aspect of the above seventh to ninth aspects, the driving control unit may set a drive limit from the drive origin when the joint part is driven, with respect to the drive part.

According to the manipulator of an eleventh aspect of the invention based on any one aspect of the above seventh to tenth aspects, the reference angle maintaining part may apply a biasing force to a rotating body that drives the joint part, and may maintain the rotational angle of the joint part at the reference angle.

According to the manipulator of a twelfth aspect of the invention based on the above eleventh aspect, the reference angle maintaining part may apply the biasing force to the joint part via the driving force transmission part.

According to the manipulator of a thirteenth aspect of the invention based on any one aspect of the above seventh to twelfth aspects, the driving force transmission part may include a linear driving force transmission member, and an initial tension application part may be further included to apply an initial tension to the driving force transmission member in order to remove loosening of the driving force transmission member in the driving force release state.

According to the manipulator of a fourteenth aspect of the invention based on any one aspect of the above seventh to thirteenth aspects, the joint part may include a bending joint, and the reference angle maintaining part may set the reference angle of the joint part including the bending joint to a rotational angle that becomes a rotational limit for allowing the operation of folding the object to be rotated coupled to the joint part.

According to a fifteenth aspect of the invention, a manipulator system is provided including the above manipulator.

BRIEF DESCRIPTION OF THE DRAWINGS

FIG. 12 is a flowchart illustrating the flow of a manipulator initialization method of the first embodiment of the invention.

FIG. 16 is a flowchart illustrating the flow of a manipulator initialization method of the second embodiment of the invention.

DETAILED DESCRIPTION OF THE INVENTION

Hereinafter, embodiments of the invention will be described with reference to the accompanying drawings. In all the drawings, even in the case of different embodiments, the same reference signs will be given to the same or equivalent members, and common description will be omitted.

First Embodiment

A manipulator and a manipulator system of a first embodiment of the invention will be described.

Figure 1:
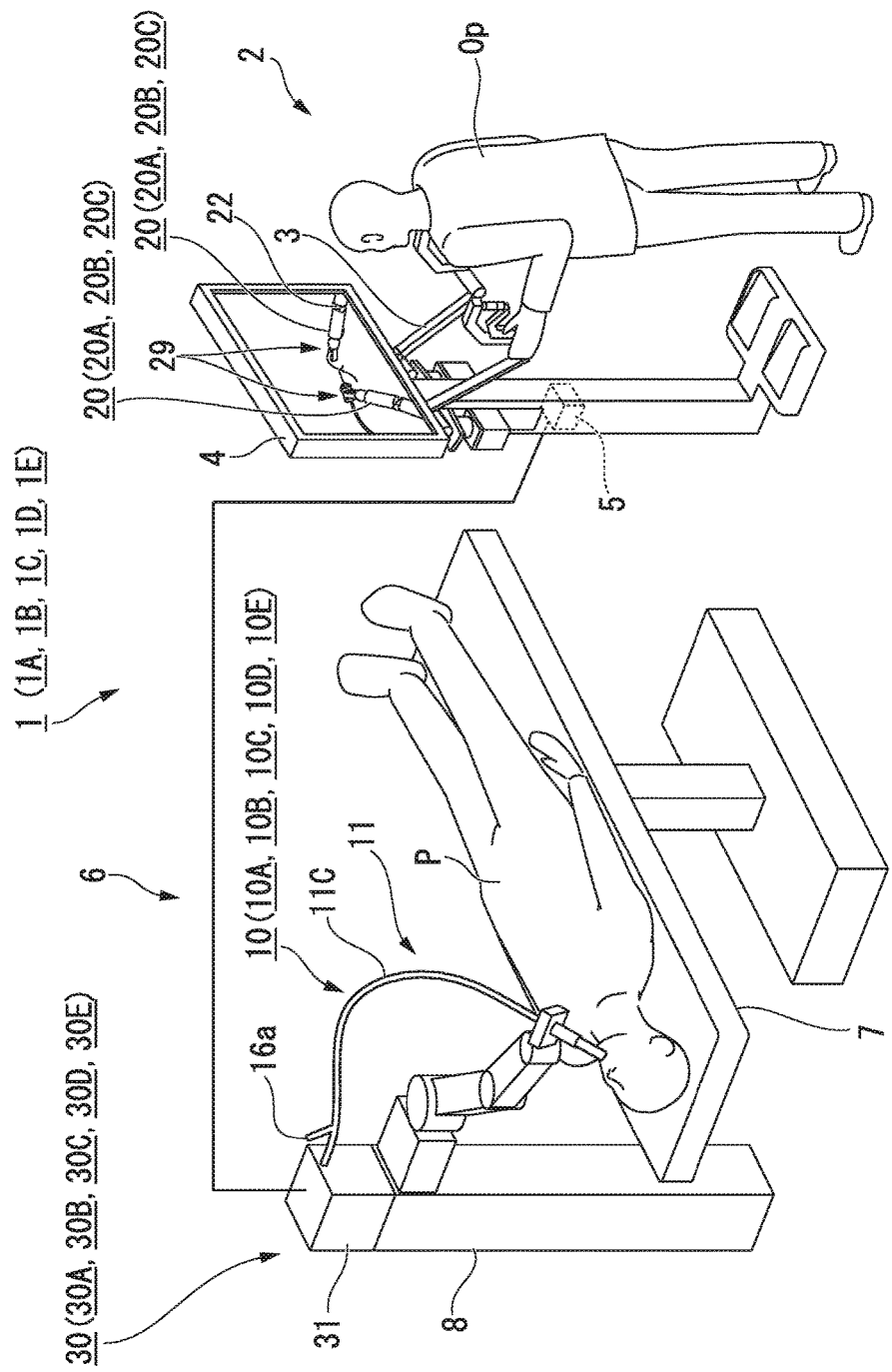
FIG. 1 is a schematic perspective view illustrating an overall configuration of a manipulator system of a first embodiment of the invention.
Figure 2A:
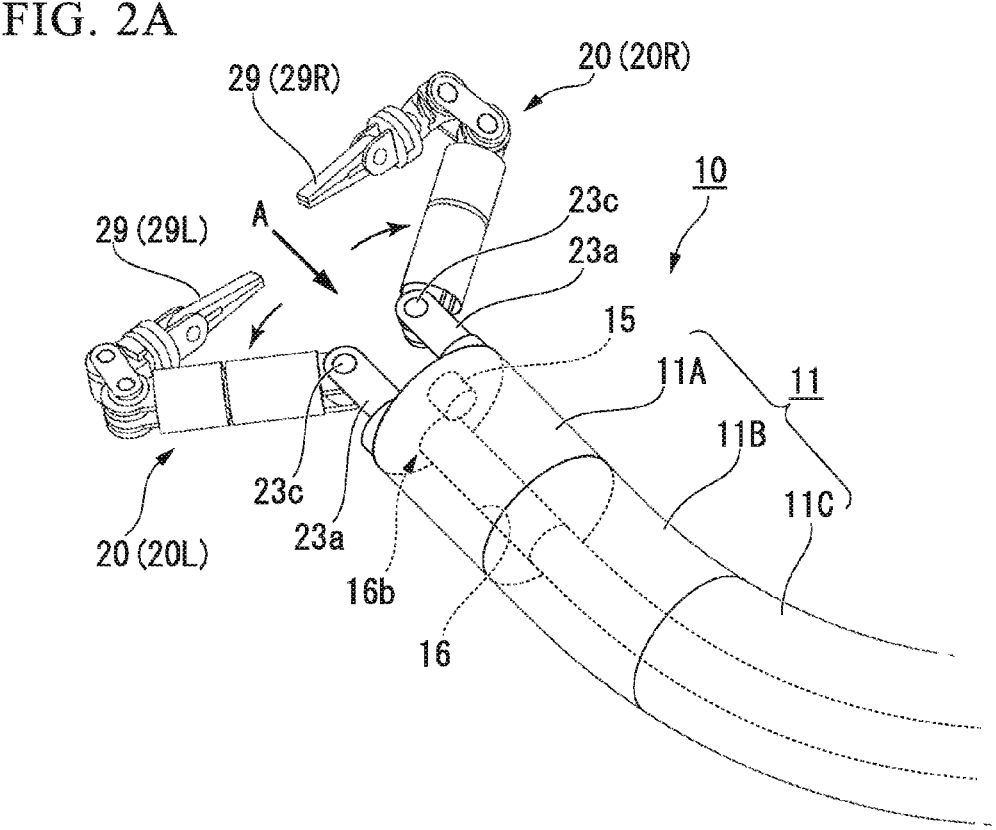
FIG. 2A is a schematic perspective view illustrating principal parts of a manipulator of the first embodiment of the invention.
Figure 2B:
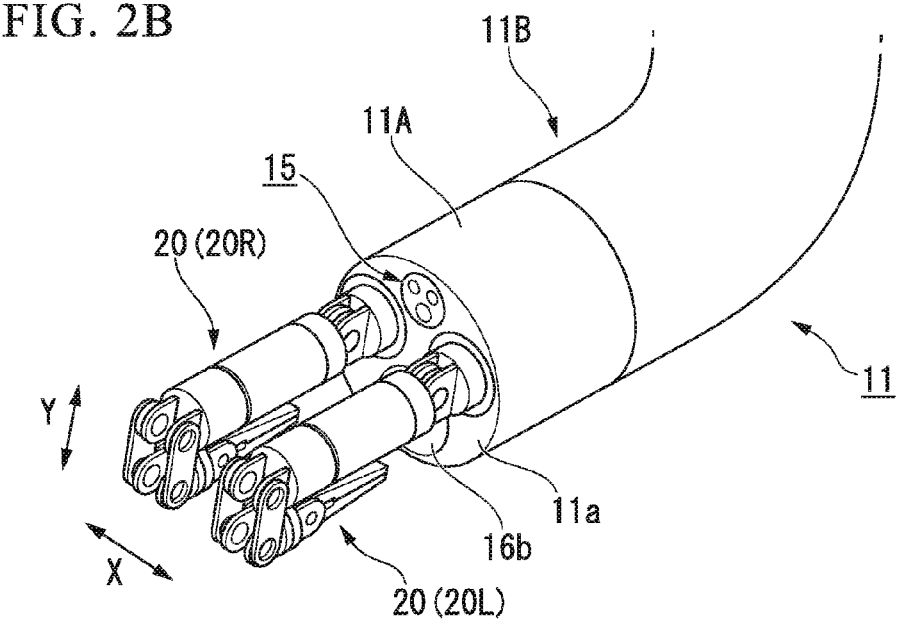
FIG. 2B is a schematic perspective view illustrating the principal parts of the manipulator of the first embodiment of the invention.
Figure 3:
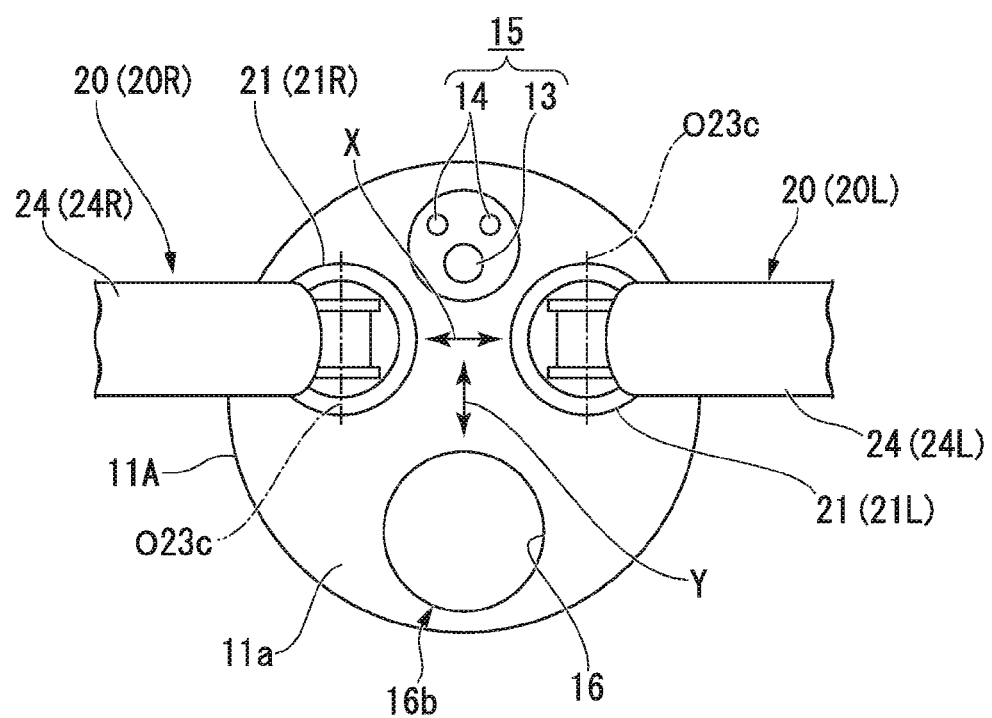
FIG. 3 is a view as seen from A in FIG. 2A.
Figure 4:
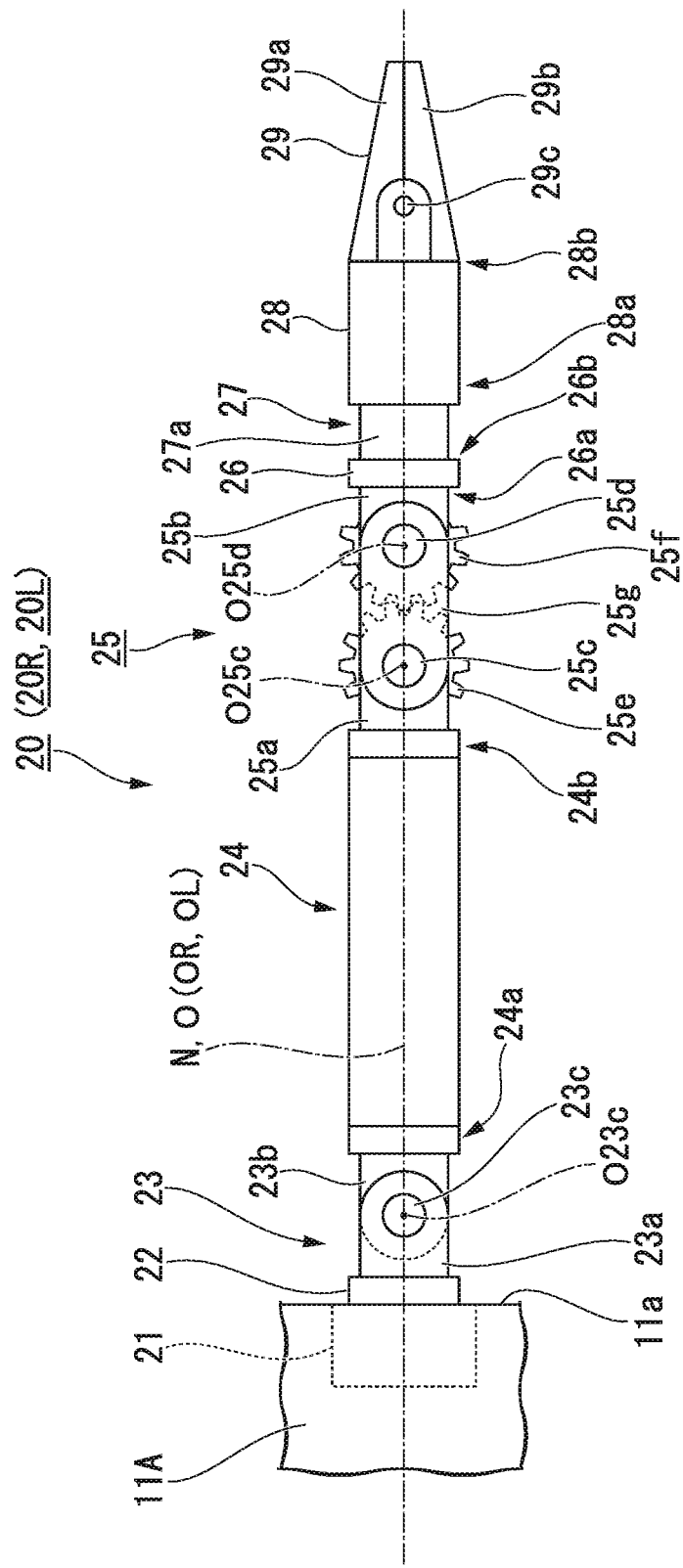
FIG. 4 is a schematic front view of the principal parts in an aligned state when the manipulator of the first embodiment of the invention is driven.
Figure 5A:
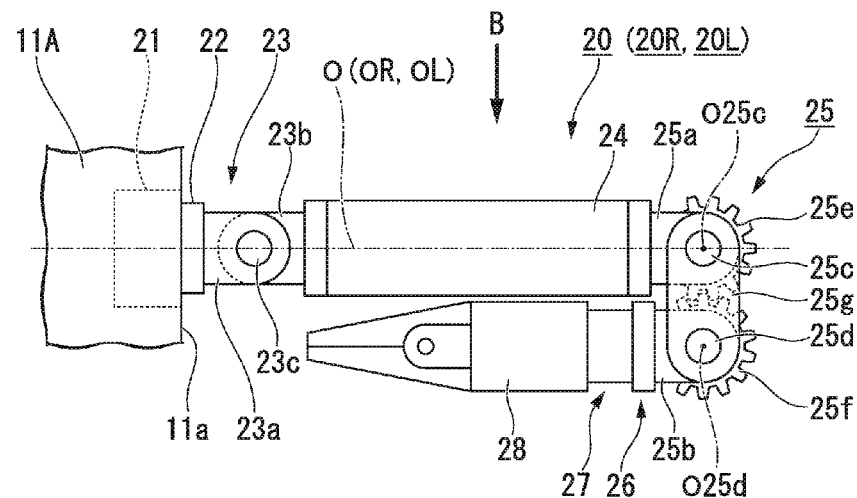
FIG. 5A is a schematic front view of the principal parts when the reference angle of the manipulator of the first embodiment of the invention is set.
Figure 5B:
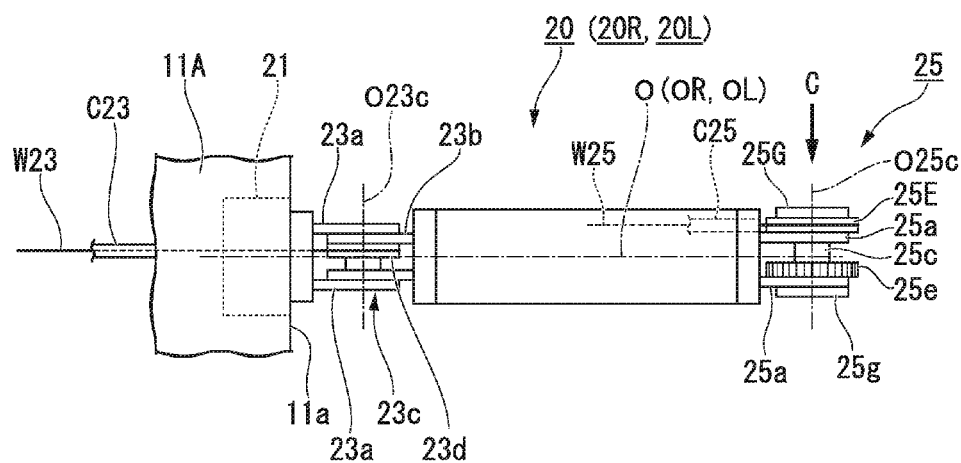
FIG. 5B is a view as seen from B of FIG. 5A.
Figure 5C:
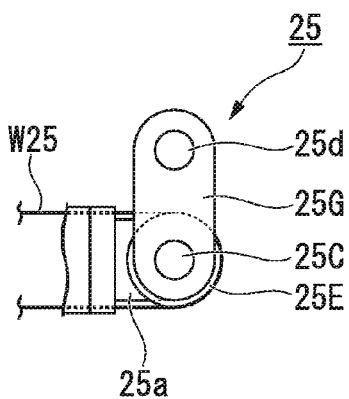
FIG. 5C is a view as seen from C of FIG. 5B.

FIG. 1 is a schematic perspective view illustrating an overall configuration of a manipulator system of a first embodiment of the invention. FIGS. 2A and 2B are schematic perspective views illustrating principal parts of a manipulator of the first embodiment of the invention. FIG. 3 is a view as seen from A in FIG. 2A. FIG. 4 is a schematic front view of the principal parts in an aligned state when the manipulator of the first embodiment of the invention is driven. FIG. 5A is a schematic front view of the principal parts when the reference angle of the manipulator of the first embodiment of the invention is set. FIG. 5B is a view as seen from B in FIG. 5A. FIG. 5C is a view as seen from C in FIG.

Figure 6:
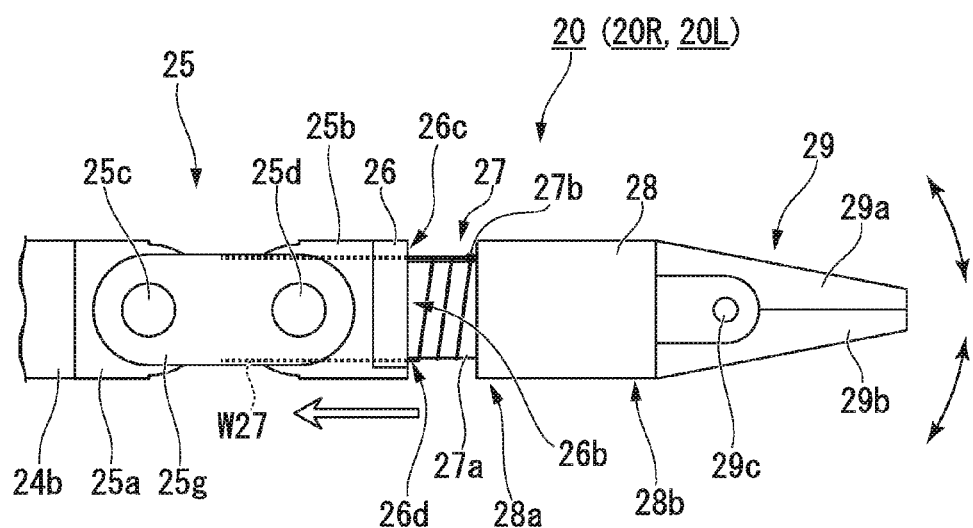
FIG. 6 is a schematic front view illustrating the configuration of a distal end part of the manipulator of the first embodiment of the invention.
Figure 7:
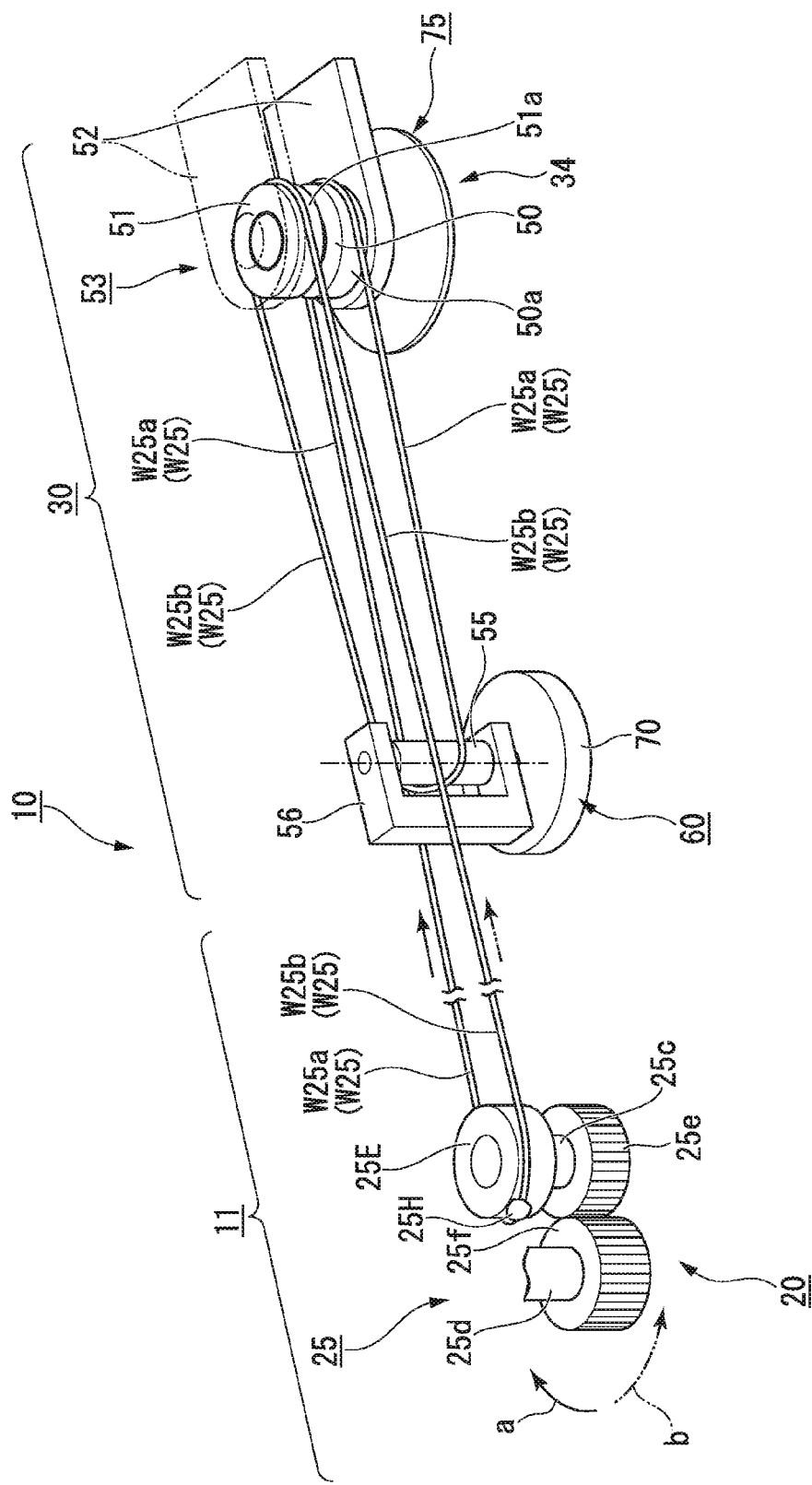
FIG. 7 is a schematic perspective view illustrating the configuration of a reference angle maintaining part of the manipulator of the first embodiment of the invention.
Figure 9:
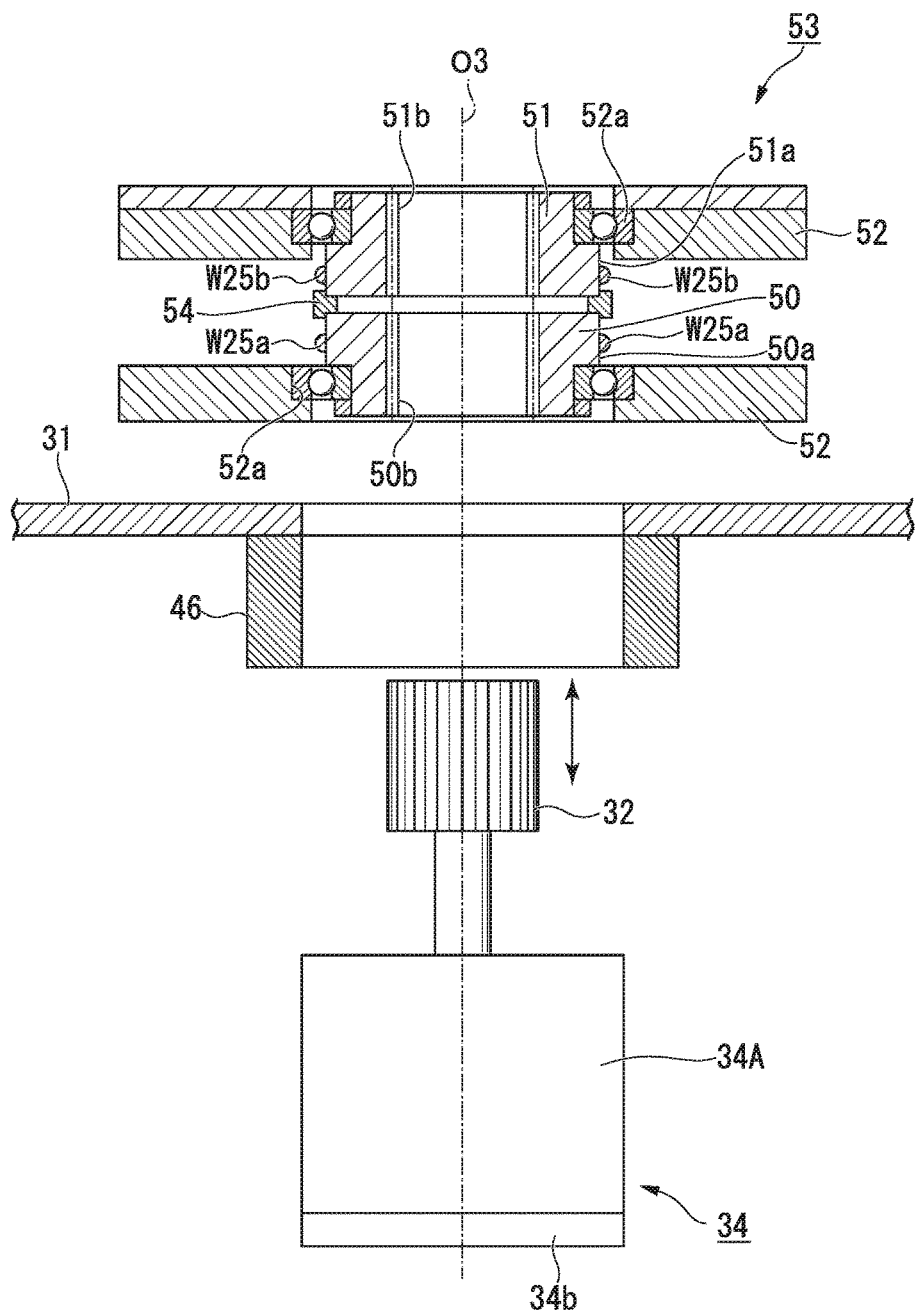
FIG. 9 is a schematic sectional view illustrating a driving force release state of the driving force relay part of the manipulator of the first embodiment of the invention.
Figure 10:
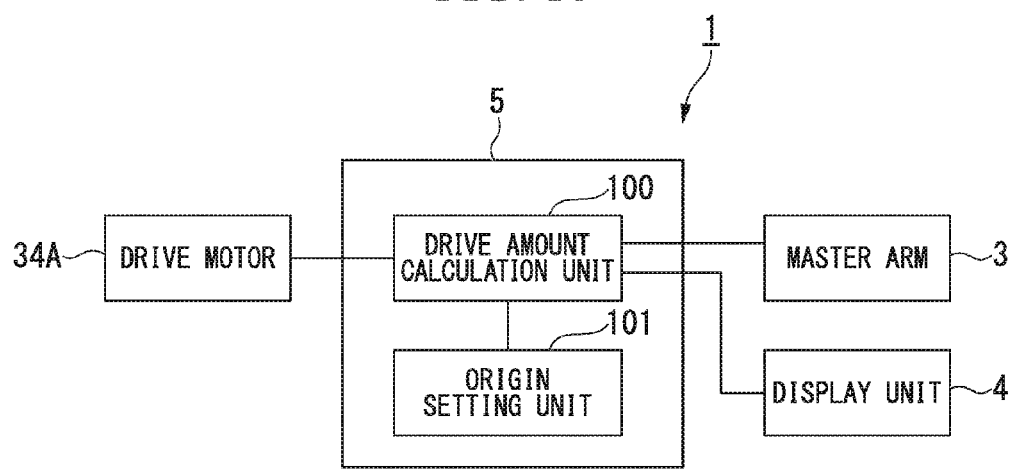
FIG. 10 is a functional block diagram of a control unit of the manipulator of the first embodiment of the invention.

5B. FIG. 6 is a schematic front view illustrating the configuration of a distal end part of the manipulator of the first embodiment of the invention. FIG. 7 is a schematic perspective view illustrating the configuration of a reference angle maintaining part of the manipulator of the first embodiment of the invention. FIGS. 8A and 8B are schematic sectional views illustrating the configuration of a drive part and a driving force relay part of the manipulator of the first embodiment of the invention. FIG. 9 is a schematic sectional view illustrating a driving force release state of the driving force relay part of the manipulator of the first embodiment of the invention. FIG. 10 is a functional block diagram of a control unit of the manipulator of the first embodiment of the invention.

In addition, since the respective drawings are schematic views, dimensions and shapes are exaggerated (the same applies to the following drawings).

As illustrated in FIG. 1, a manipulator system 1 of the present embodiment is a so-called master/slave type system including a master manipulator 2 operated by an operator Op, and a slave manipulator 6 provided with an endoscope apparatus 10 for treatment.

The master manipulator 2 includes a master arm 3 with which the operator Op performs an operation input, a display unit 4 that displays an image or the like captured using the endoscope apparatus 10 for treatment, and a control unit 5 that generates an operation command for operating the slave manipulator 6 on the basis of the operation of the master arm 3.

In the present embodiment, the master arm 3 is an operating part for operating respective parts of the slave manipulator 6 (manipulator) including a holding arm part 20 (medical instrument) (to be described below) that is attached to the endoscope apparatus 10 (manipulator) for treatment. Additionally, although not illustrated in detail, the master manipulator 2 has a pair of the master arms 3 corresponding to the right hand and left hand of the operator Op.

The master arm 3 has a joint structure in order to operate a manipulator having one or more joint parts like a bending part 11B and the holding arm part 20 of the endoscope apparatus 10 for treatment (to be described below).

Additionally, an end part of the master arm 3 located on the operator Op side is provided with a grasp operating part (not illustrated) for operating a grasping part 29 (to be described below) of the holding arm part 20.

The display unit 4 is a device on which an image of a treatment target part captured by an observation unit 15 (refer to the FIGS. 2A and 2B; to be described below) attached to the endoscope apparatus 10 for treatment, an operation screen required for operation, the information from the control unit 5, and the like are displayed. The holding arm part 20 together with the treatment target part is also displayed on the display unit 4.

The slave manipulator 6 has a placement table 7 on which a patient P is placed, a multi joint robot 8 arranged in the vicinity of the placement table 7, and the endoscope apparatus 10 for treatment.

The multi joint robot 8 and the endoscope apparatus 10 for treatment operate according to an operation command issued from the master manipulator 2.

However, in the manipulator system of the invention, the multi joint robot is not indispensable, and for example, a configuration in which an assistant (not illustrated) holds the endoscope apparatus 10 for treatment may be adopted.

As illustrated in FIG. 1, the endoscope apparatus 10 for treatment has an overtube 11 that is an elongated member for being inserted into a body of the patient P, and a drive unit 30 that supplies a driving force to the overtube 11.

As illustrated in FIG. 2A, the overtube 11 includes a tubular insertion part 11C having flexibility, the well-known bending part 11B equipped with, for example, joint rings, bending pieces, and the like, and a distal end part 11A formed of a columnar rigid material, in this order from a proximal end toward a distal end.

The bending part 11B can change the orientation of the distal end part 11A by being bent by an operation input to the master arm 3. As a mechanism for bending the bending part 11B, for example, a well-known configuration in which driving wires inserted through inner peripheral surfaces of joint rings and bending pieces and fixed to the distal end part 11A can be inserted through the insertion part 11C and pulled with drive motors or the like on the proximal end side can be adopted.

A treatment tool channel 16 that forms a tubular path that supplies a treatment tool is provided inside the overtube 11.

A base end part (proximal end side) of the treatment tool channel 16, as illustrated in FIG. 1, is connected to a supply port 16a that opens to the side of the insertion part 11C.

A distal end part 16b of the treatment tool channel 16 passes through the distal end part 11A in an axial direction, and as illustrated in FIG. 3, opens to a distal end surface 11a of the distal end part 11A.

The treatment tool channel 16 is constituted of a tubular member having flexibility inside the bending part 11B and the insertion part 11C.

As illustrated in FIG. 3, the distal end surface 11a of the distal end part 11A is provided with the observation unit 15 and the holding arm part 20.

The observation unit 15 is a device for observing a treatment target part, and includes a well-known imaging mechanism 13 and a well-known illumination mechanism 14.

The imaging mechanism 13 and the illumination mechanism 14 are arranged inside the distal end part 11A, electrical wiring and optical fibers (not illustrated) are inserted through the inside of the bending part 11B and the inside of the insertion part 11C, and are coupled to an electric circuit and a light source in the control unit 5 (to be described below).

The imaging mechanism 13 and the illumination mechanism 14 both have optical opening windows, in the distal end surface 11a of the distal end part 11A, and the outside light in front of the distal end part 11A can be received through the opening windows, or illumination light can be emitted forward therethrough.

In addition, in the present embodiment, the observation unit 15 of the endoscope apparatus 10 for treatment is described to be fixed to a distal end part of the overtube 11. However, the observation unit 15 may be movably provided.

For example, an endoscope for observation having an observation unit at a distal end thereof is inserted through the treatment tool channel 16 of the overtube 11, and the observation unit is made to protrude from the overtube 11, so that the position and the orientation of the observation unit 15 can be changed by a forward and backward movement operation and a bending operation of the inserted endoscope.

As illustrated in FIG. 2A, the holding arm part 20 is an example of a medical instrument that includes a multi joint structure having at least one joint part and a shaft-shaped part coupled to this joint part, and drives the joint part, thereby moving or driving an end effector provided at a distal end thereof.

The holding arm part 20 can be used as a manipulator by being connected with the drive unit 30 (referring to FIG. 1) together with the overtube 11 as in the present embodiment.

In the present embodiment, the holding arm part 20 is formed in the shape of an elongated shaft as a whole, and has a grasping part 29 as the end effector.

In the present embodiment, a pair of the holding arm parts 20 that have the same configuration are arranged in parallel. In the following, in a case where the holding arm parts need to be distinguished from each other, these holding arm parts are referred to as holding arm parts 20R and 20L. Additionally, even in a case where it is necessary to distinguish respective parts that constitute each holding arm part 20 from each other, the respective parts are distinguished from each other by attaching subscripts R and L to reference signs.

However, in order to make description simple in the drawings, the subscripts R and L are omitted in some members in a case where a correspondence relationship is easily known.

As illustrated in FIG. 4, each holding arm part 20 includes a first rotation joint part 21 (joint part), a first shaft-shaped part 22 (a shaft-shaped part, an object to be rotated), a first bending joint part 23 (a joint part, a bending joint), a second shaft-shaped part 24 (a shaft-shaped part, an object to be rotated), a second bending joint part 25 (a joint part, a bending joint), a third shaft-shaped part 26 (a shaft-shaped part, an object to be rotated), a second rotation joint part 27 (joint part), a fourth shaft-shaped part 28 (a shaft-shaped part, an object to be rotated), and the grasping part 29, in order from a base end side toward a distal end side.

Hereinafter, for simplicity, if there is no concern of misunderstanding in a case where the first rotation joint part 21, the first bending joint part 23, the second bending joint part 25, and the second rotation joint part 27 are generically named, these may simply be referred to as joint parts of the holding arm part 20. Similarly, in a case where the first shaft-shaped part 22, the second shaft-shaped part 24, the third shaft-shaped part 26, and the fourth shaft-shaped part 28 are generically named, these may simply be referred to as shaft-shaped parts of the holding arm part 20.

All of the respective joint parts of the holding arm part 20 are coupled to the drive unit 30 (refer to FIG. 1), which is provided at a base end part of the overtube 11 and is described below, by driving wires (not illustrated) that are driving force transmission members, and are able to be independently driven by the drive unit 30.

In addition, since the holding arm part 20 has multiple degrees of freedom depending on the respective joint parts, the relative positions of the respective members vary depending on drive states.

In the following, in a case where the configuration and arrangement of the respective parts are described, and unless otherwise mentioned, as illustrated in FIG. 4, a relative positional relationship will be described supposing the respective parts are in a drive state (referred to as an aligned state) where these parts extend straight along a normal line N of the distal end surface 11a of the distal end part 11A.

In addition, such an aligned state is an origin orientation of the holding arm part 20 obtained by performing an origin setting step to be described below, in the present embodiment.

The first rotation joint part 21 is a rotation joint that is fixed to the distal end part 11A, and rotates the first shaft-shaped part 22 coupled to the distal end side around a rotational axis O parallel to the normal line N of the distal end surface 11a.

The first rotation joint part 21 has a well-known configuration in which a driving wire (not illustrated) wound around an outer peripheral part of a base end part of the first shaft-shaped part 22 is rotationally driven by being pulled with the drive unit 30.

The first shaft-shaped part 22 is a shaft-shaped member that is a short shaft in which a base end part (not illustrated) is rotatably supported by the first rotation joint part 21.

The first bending joint part 23 is a bending joint including a support part 23a fixed to a distal end part of the first shaft-shaped part 22, and a turning part 23b rotatably coupled to the support part 23a by a turning shaft 23c that extends in a direction orthogonal to the rotational axis O.

As illustrated in FIG. 5B, a pulley 23d to which an end part of a driving wire W23 (linear driving force transmission member) is joined is fixed to the turning part 23b.

The driving wire W23 is inserted through the inside of the overtube 11 in a state where the driving wire is inserted through a sheath C23, and is extended to the drive unit 30.

For this reason, the first bending joint part 23 can turn around a rotational axis O23 that is a central axis of the turning shaft 23c by pulling the driving wire W23 with the drive unit 30.

As illustrated in FIG. 4, the second shaft-shaped part 24 is an elongated tubular member to which a base end part 24a is fixed to the turning part 23b of the first bending joint part 23. The second shaft-shaped part 24 is arranged coaxially with the rotational axis O in the in the aligned state.

As illustrated in FIGS. 5A, 5B, and 5C, the second bending joint part 25 is a bending joint including a support part 25a fixed to a distal end part 24b of the second shaft-shaped part 24, a rotating shaft 25c that is rotatably inserted through the support part 25a and extends along a rotational axis O25c parallel to the rotational axis O23, a rotating shaft 25d arranged parallel to the rotating shaft 25c, a pair of turning supporting plates 25g and 25G that turnably supports the rotating shaft 25c and 25d with a certain distance from each other, and a turning part 25b turnably coupled to the turning supporting plates 25g and 25G by the rotating shaft 25d.

As illustrated in FIGS. 5B and 5C, a drive pulley 25E that transmits a driving force to the second bending joint part 25 at a position coaxial with the rotating shaft 25c is fixed to the turning supporting plate 25G.

A driving wire W25 (linear driving force transmission member) is hung around the drive pulley 25E. The driving wire W25 is inserted through the inside of the second shaft-shaped part 24 and the inside of the overtube 11 in a state where this driving wire is inserted through a sheath C25, and is extended to the drive unit 30.

Accordingly, if the driving wire W25 is pulled on the base end side of the holding arm part 20, the drive pulley 25E rotates around the rotating shaft 25c, and the turning supporting plate 25G also turns together with the drive pulley 25E.

In this case, the turning supporting plate 25g moves similar to the turning supporting plate 25G through which the rotating shafts 25c and 25d are inserted. In addition, wiring of the driving wire W25 will be described below in detail.

A guide gear 25e having as a pitch circle radius of half of an inter-axial distance between the rotating shafts 25c and 25d is fixed to the support part 25a that the turning supporting plate 25g approaches, so as to become coaxial with the rotating shaft 25c. As illustrated in FIG. 5A, a coupling gear 25f having the same pitch circle radius as the guide gear 25e is fixed to the turning part 25b that the turning supporting plate 25g approaches.

The coupling gear 25f is arranged to face the guide gear 25e in a radial direction, and is fixed in a state where this coupling gear meshes with the guide gear 25e.

By virtue of such a configuration, in the second bending joint part 25, the support part 25a and the turning supporting plates 25g and 25G turn around the rotating shaft 25c and are thereby bent at their respective positions, and the turning supporting plates 25g and 25G and the turning part 25b turn around the rotating shaft 25d and are thereby bent at their respective positions.

In this case, since the turning part 25b turns together with the coupling gear 25f that rolls on a pitch circle of the guide gear 25e without slipping, this turning part rotates by an angle that is twice as large as the rotational angle of the turning supporting plates 25g and 25G with respect to the rotational axis O.

As illustrated in FIG. 4, the third shaft-shaped part 26 is a shaft-shaped member that is a short shaft in which a base end part 26a is fixed to the turning part 25b of the second bending joint part 25. The third shaft-shaped part 26 is arranged coaxially with the rotational axis O in the aligned state.

The second rotation joint part 27, as illustrated in an enlarged manner in FIG. 6, includes a tubular part 27a that is rotatably supported around the rotational axis O in the aligned state with respect to a distal end part 26b of the third shaft-shaped part 26.

An end part of a driving wire W27 (linear driving force transmission member, not illustrated in FIGS. 4, 5A, and 5B) is fixed to a wire junction part 27b on an outer peripheral surface of the tubular part 27a. The driving wire W27 is spirally wound so as to go around the outer peripheral surface of the tubular part 27a, and is inserted through holes 26c and 26d that pass through the third shaft-shaped part 26 in the axial direction.

The driving wire W27 is inserted through the inside of the second bending joint part 25, the inside of the second shaft-shaped part 24, and the inside of the overtube 11 in a state where this driving wire is inserted through a sheath (not illustrated), and is extended to the drive unit 30.

For this reason, if the driving wire W27 is pulled, the tubular part 27a of the second rotation joint part 27 rotates around a central axis of the third shaft-shaped part 26. Additionally, a rotational direction can be changed by changing the pulling direction of the driving wire W27.

The fourth shaft-shaped part 28 is a tubular member in which a base end part 28a is fixed coaxially with the tubular part 27a in a distal end part of the tubular part 27a of the second rotation joint part 27.

Here, an example of rotational limits of each joint part in the present embodiment will be described.

The rotatable range of the first rotation joint part 21 is ±90°.

Here, as for rotational angles showing the rotational limits, as illustrated in FIG. 3, when, within a plane parallel to the distal end surface 11a of the distal end part 11A, a direction in which the first rotation joint parts 21R and 21L face each other is defined as an X direction and a direction orthogonal to the X-direction is defined as a Y direction, the rotational angle of the rotational axis O23 of the first bending joint part 23 in a state along the Y direction is 0° (refer to FIG. 3), and the rotational angle thereof in a state along the X direction is 90°.

As for the positive and negative of the rotational angles, on the basis of 0°, in the illustration of FIG. 3, the counterclockwise direction is defined as positive in the first rotation joint part 21R, and the clockwise direction is defined as positive in the first rotation joint part 21L.

The rotatable range of the first bending joint part 23 is −30° to −90°.

Here, 0°, as illustrated in FIG. 4, is the rotational angle of the first bending joint part 23R (23L) in a case where the central axis of the second shaft-shaped part 24R (24L) is aligned with the rotational axis OR (OL).

90° is the rotational angle of the first bending joint part 23R (23L) in a case where the central axis of the second shaft-shaped part 24R (24L) is orthogonal to the rotational axis OR (OL).

As for the positive and negative of the rotational angle of the first bending joint part 23, for example, as indicated by a curved arrow of FIG. 2, when the first rotation joint part 21 is at the position of 0°, a direction in which the second shaft-shaped parts 24R and 24L are separated from each other from a state where the first bending joint part 23 is the above 0° is measured as positive.

The rotatable range of the second bending joint part 25 is ±90° around the rotational axis O25c, and ±90° around the rotational axis O25d, and the rotational range of the entire second bending joint part 25 is ±180°.

Here, the positive direction of the angle is the same as the positive direction of the angle of the first bending joint part 23.

In addition, the rotational angle of the "entire second bending joint part 25" means an angle formed between a central axis of the support part 25a and a central axis of the turning part 25b.

The rotatable range of the second rotation joint part 27 is ±180°.

Here, as illustrated in FIG. 4, a positional relationship in which a turning shaft 29c of the grasping part 29 fixed to the fourth shaft-shaped part 28 becomes parallel to the rotational axis O25c of the second bending joint part 25 and O25d is 0°, and a twisted position where the turning shaft 29c is orthogonal to the rotational axes O25c and O25d is 90°.

Although the positive and negative of the rotational angle of the second rotation joint part are not particularly limited, for example, it is possible to adopt the same directions as those of the first rotation joint part 21.

The grasping part 29 is an end effector of the holding arm part 20, and is attached to a distal end part 28b of the fourth shaft-shaped part 28.

The configuration of the grasping part 29 has a pair of grasping members 29a and 29b for grasping an object to be grasped, and the turning shaft 29c that turnably supports the grasping members 29a and 29b.

By operating the grasp operating part (not illustrated) for the master arm 3, the grasping members 29a and 29b are turned about the turning shaft 29c, and are moved like an arrow of FIG. 6 to perform an opening/closing operation.

Transmission means for transmitting the driving force of the grasping part 29 is not particularly limited, and for example, means for driving a link (not illustrated) coupled to the grasping members 29a and 29b with an operating wire (not illustrated) is possible.

In the drive unit 30, as illustrated in FIG. 1, a housing part 31 is provided at a base end part of the insertion part 11C.

A driving coupling part 53 (driving force relay part), a reference angle maintaining part 60, and a drive motor part 34 (drive part), which are illustrated in FIG. 7, are included inside the housing part 31.

In addition, although a set of the driving coupling part 53, the reference angle maintaining part 60, and the drive motor part 34 is provided according to each joint part, all of them have the same configuration. In the following, an example in a case of the second bending joint part 25 will be described.

Although this second bending joint part is different from the other joint parts in that it does not include the guide gear 25e and the coupling gear 25f, the operation of the drive pulley and the driving wires is the same. For example, the drive pulley 25E and the driving wire W25 in the following description may be replaced with the pulley 23d and the driving wire W23 in the case of the first bending joint part 23, and may be replaced with the tubular part 27a and the driving wire W27 in the case of the second rotation joint part 27. For this reason, the description of the operation of the other joint parts will be omitted.

As illustrated in FIG. 7, the driving coupling part 53 includes a first internal gear 50 and a second internal gear 51 around which the driving wire W25 is wound in order to pull the driving wire W25.

The first internal gear 50 (second internal gear 51) has an outer peripheral surface 50a (51a) for allowing the driving wire W25 to be wound therearound, and is housed in a gear case 52 fixed to the housing part 31 (refer to FIG. 1).

In addition, in the present embodiment, an end part of the driving wire W25 is fixed at a position (not illustrated) on the outer peripheral surface 50a (51a) so that the rotation of the first internal gear 50 (second internal gear 51) is reliably transmitted to the driving wire W25. Accordingly, it is possible to reliably pull the driving wire W25 without causing any slip or the like even in a case where large loosening has occurred in the driving wire W25.

However, for example, in a case where no slip is caused only by frictional engagement, a configuration in which the driving wire is not fixed to the outer peripheral surface 50a (51a) is also possible.

Both end parts of the driving wire W25 on the side of a joint part 22B are fixed to a drive pulley 25E in a junction part 25H after being wound around the drive pulley 25E of the of the second bending joint part 25.

An intermediate part of the driving wire W25 is wound around the outer peripheral surface 50a of the first internal gear 50 of the driving coupling part 53, a pulley 55 (to be described below) of the reference angle maintaining part 60, and the outer peripheral surface 51a of the second internal gear 51 in this order.

In addition, since FIG. 7 is a schematic view, the driving wire W25 is shown so as to be wound around the outer peripheral surfaces 50a and 51a by about a semiperimeter. However, this is an example, and the number of times of winding is not limited to about a semiperimeter. For example, an appropriate number of times of winding that is a semiperimeter or less or a semiperimeter or more is possible.

Similarly, a different number of times of winding from the illustration is possible with respect to the pulley 55. Particularly, the pulley 55 receives a biasing force resulting from a spiral spring 70 to be described below. Since the driving wire W25 is only frictionally engaged, it is preferable to wind the driving wire so that the winding angle becomes greater so as not to slip easily. Additionally, it is more preferable to wind the driving wire about 1 round or more.

In the following, with the location of the driving wire W25 wound around a central part of the pulley 55 as a center, a portion that faces the drive pulley 25E via the first internal gear 50 from the pulley 55 is referred to as a first wire part W25a, and a portion that faces the drive pulley 25E via the second internal gear 51 from the pulley 55 is referred to as a second wire part W25b.

Figure 8:
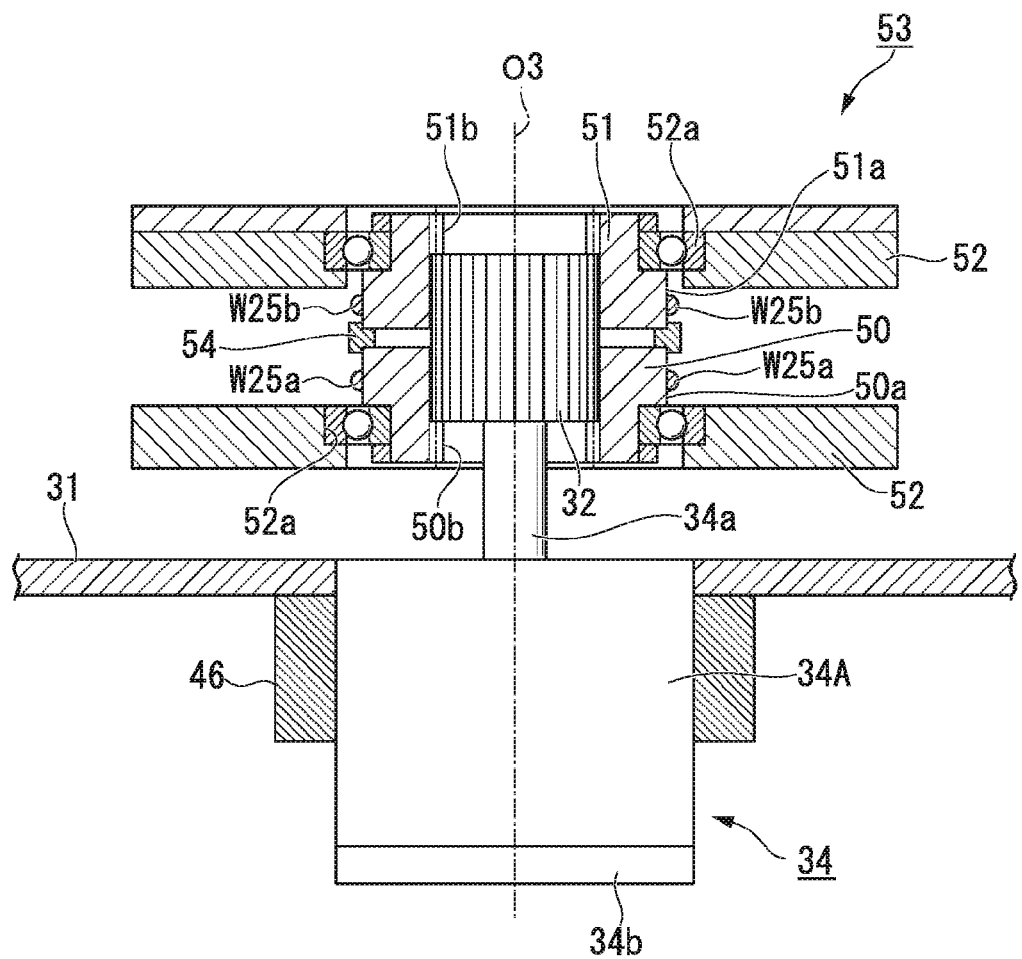
FIG. 8 is a schematic sectional view illustrating the configuration of a drive part and a driving force relay part of the manipulator of the first embodiment of the invention.

As illustrated in FIG. 8, the first internal gear 50 and the second internal gear 51 are rotatably supported by a bearing 52a provided in the gear case 52, and a mutual positional relationship is fixed in an axially separated state by a washer 54. For this reason, the first internal gear 50 and the second internal gear 51 can be rotated about a rotation center O3 in synchronization with each other.

As the bearing 52a, for example, a ball bearing can be adopted.

Internal-teeth parts 50b and 51b which a pinion 32 of the drive motor part 34 (to be described below) is insertable into in the axial direction and is engageable with in the circumferential direction are formed coaxially with the rotation center axis O3 at central parts of the first internal gear 50 and the second internal gear 51.

The drive motor part 34 includes a drive motor 34A that generates a driving force for pulling the driving wire W25, and the pinion 32 fixed to a distal end part of an output shaft 34a of the drive motor 34A coaxially with the output shaft 34a.

The type of drive motor 34A is not particularly limited if only the output shaft 34a can be rotated by a predetermined amount of rotation on the basis of a driving command value. For example, a servo motor, a stepping motor, a DC motor, and the like can be adopted.

In the present embodiment, the drive motor 34A has an encoder 34b that detects the rotational amount of the output shaft 34a, and is communicably connected to the control unit 5 that controls the driving of the drive motor 34A on the basis of the operation of the master arm 3.

The pinion 32 is a gear that has a tooth form in which the pinion 32 meshes with the internal-teeth parts 50b and 51b of the first internal gear 50 and the second internal gear 51 at a position coaxial therewith. The face width of the pinion 32 is a face width such that the pinion 32 can mesh simultaneously with the internal-teeth parts 50b and 51b.

The drive motor part 34 with such a configuration is detachably fixed to a fixing part 46 provided in the housing part 31 in a positioned state in an outer peripheral part of the drive motor 34A. An attachment/detachment direction of the drive motor part 34 is a direction along the rotation center axis O3.

The configuration of the fixing part 46 is not particularly limited if such attachment and detachment are possible. For example, instances such as a configuration in which a projection part to which an elastic force is biased is provided, and is detachably engaged to a recessed part formed in an outer peripheral part of the drive motor 34A, and a configuration in which a clamp member that fixes the position of the drive motor 34A is provided, and the position of the clamp member is fixed by a screw or a concavo-convex fitting mechanism can be included.

In addition, it is not indispensable to individually detach and attach the drive motor 34A in this way. For example, in a case where a plurality of the drive motors 34A are provided, a configuration in which a holding member that integrally holds the plurality of drive motors 34A is provided, and the holding member is attachable to and detachable from a suitable fixing part provided in the housing part 31 is also possible. In this case, the plurality of drive motors 34A are simultaneously detached and attached.

In FIG. 8, a state where the drive motor part 34 is mounted on the fixing part 46 is shown. In contrast, in FIG. 9, a state where the drive motor part 34 is detached from the fixing part 46 is shown.

In the following description, in a case where the positional relationship of the drive motor part 34 with respect to the driving coupling part 53 is described, a positional relationship in the mounting state of the drive motor part 34 will be described unless particularly mentioned.

Such a drive motor part 34 can be extracted and detached along the rotation center axis O3 as illustrated in FIG. 9 by releasing the fixation thereof to the fixing part 46.

The driving force release state where a driving force is cut off is formed in a state where the drive motor part 34 is extracted and detached from the driving coupling part 53 in this way.

Additionally, the drive motor part 34 can be mounted on the fixing part 46 by being conversely pushed in along the rotation center axis O3. If the drive motor part 34 is mounted on the fixing part 46, the axial position of the drive motor part 34 is determined, and as illustrated in FIG. 8, the pinion 32 meshes with the internal-teeth parts 50b and 51b by almost the same width as the internal-teeth parts.

A driving force relay state where a driving force is relayed to the first internal gear 50 and the second internal gear 51 is formed in a state where the drive motor part 34 is mounted on the driving coupling part 53 in this way.

For this reason, the driving coupling part 53 constitutes the driving force relay part capable of being switched between the driving force relay state and the driving force release state.

As illustrated in FIG. 7, the reference angle maintaining part 60 includes a pulley 55 that has the intermediate part of the driving wire W25 wound around an outer peripheral surface thereof, a pulley holding part 56 that rotatably holds the pulley 55, and a spiral spring 70 that is coupled coaxially with the pulley 55 and generates a biasing force that rotates the pulley 55 in one direction.

By virtue of such a configuration, the first internal gear 50, the second internal gear 51, the pulley 55, and the driving wire W25 constitute a driving force transmission part that transmits a driving force from the drive motor part 34 that is a drive part in the drive unit 30 to the second bending joint part 25.

Next, with respect to the functional configuration of the control unit 5, the functional configuration of portions (driving control units) that control the driving of the holding arm part 20 will mainly be described.

The control unit 5, as illustrated in FIG. 10, includes a drive amount calculation unit 100 and an origin setting unit 101 as driving control units.

The drive amount calculation unit 100 analyzes the movement of the joint part of the master arm 3 sent from the master arm 3 to calculate the rotational angle of each joint part of the holding arm part 20 for performing the same operation, and sends a corresponding driving command value to each drive motor 34A that drives each joint part of the holding arm part 20.

The origin setting unit 101 sends a control signal for calculating a driving command value corresponding to the amount of driving that rotates each joint part by a predetermined angle from a reference angle, and a driving position of each drive motor 34A of which this movement is completed is set in the drive amount calculation unit 100 as an origin of the driving command value that the drive amount calculation unit 100 sends to the drive motor 34A.

In the present embodiment, such origin setting is performed by the origin setting unit 101 when the origin setting unit 101 is notified of being brought into the driving force release state by notification means (not illustrated).

Such notification means may include, for example, means such as a detection sensor that detects a mounting state in an interlocking manner with the attachment and detachment of the drive motor part 34, and means for manually performing notification with a pushbutton switch after the operator Op has finished mounting. The type of detection sensor may include, for example, instances of mechanical sensors, such as an optical sensor and a pushing switch, and detection sensors using an electrical field and a magnetic field.

In the present embodiment, although illustration is omitted, a detection sensor interlocked with the operation of mounting the drive motor part 34 on the fixing part 46 is provided, and the origin setting unit 101 is notified of being brought into the driving force relay state by the output of the detection sensor.

In the present embodiment, if the origin setting unit 101 sets the origin, a drive limit to each joint part of the holding arm part 20 is set.

The drive limit is determined in advance with respect to each joint part of the holding arm part 20, and the origin setting unit 101 soft-sets each drive limit in the drive amount calculation unit 100 communicably connected thereto.

On the other hand, the drive amount calculation unit 100 performs the operation of determining whether or not the driving command value exceeds the drive limit before the driving command value is sent to the drive motor 34A.

In a case where the driving command signal is determined to exceed the drive limit, the drive amount calculation unit 100 stops the driving of the drive motor 34A, and displays information capable of knowing that the driving command value exceeds the drive limit on the display unit 4.

The device configuration of such a control unit 5 consists of a computer consisting of a CPU, a memory, an input/output interface, an external storage, and the like, and thereby, a suitable control program that realizes the control functions as above is performed.

Next, the operation of the holding arm part 20 in the endoscope apparatus 10 for treatment will be described. Similar to the above description, the operation of the second bending joint part 25 will mainly be described as an example.

Figure 11A:
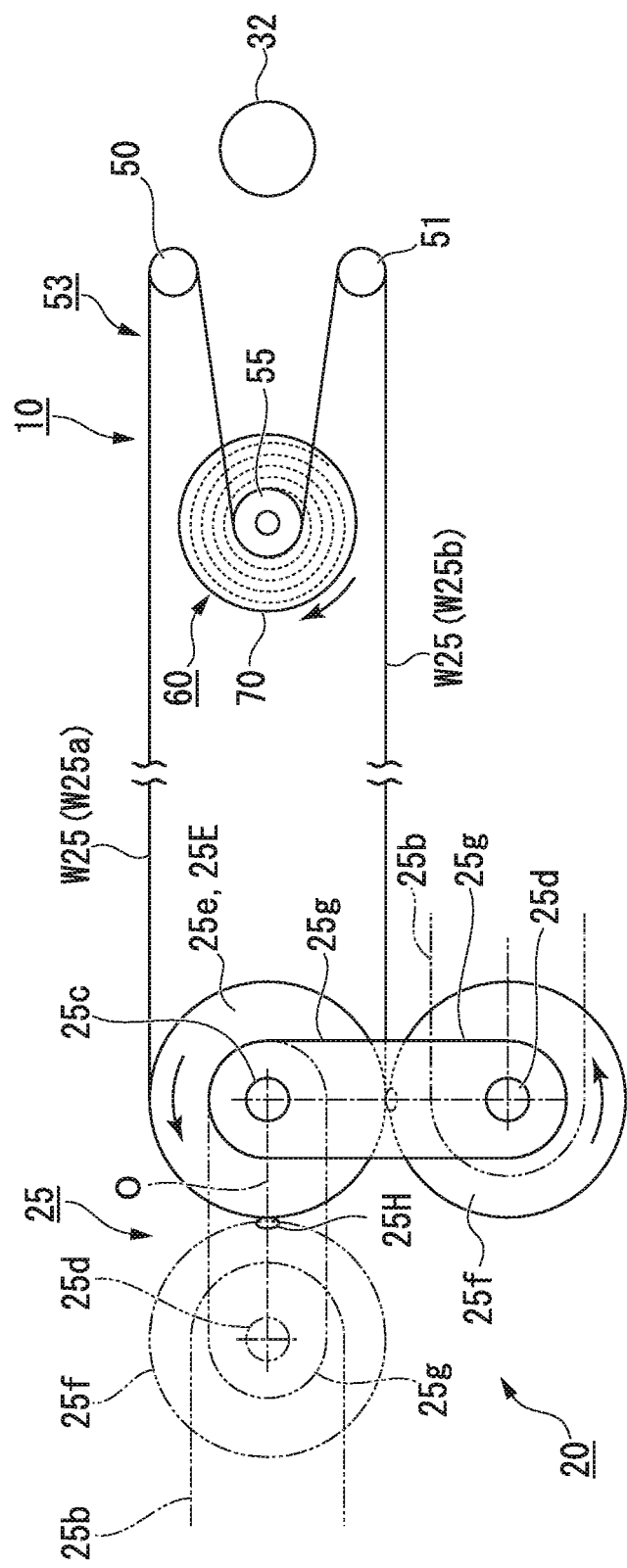
FIG. 11A is a schematic explanatory view of the operation of the manipulator of the first embodiment of the invention.
Figure 11B:
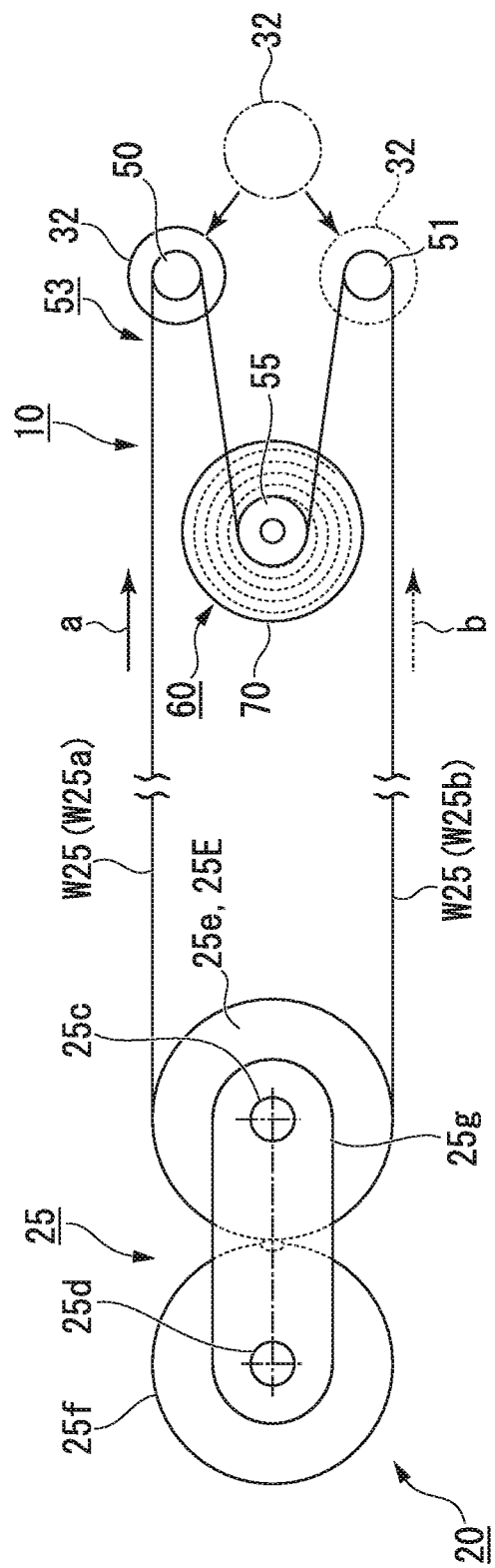
FIG. 11B is a schematic explanatory view of the operation of the manipulator of the first embodiment of the invention.

FIGS. 11A and 11B are schematic explanatory views of the operation of the manipulator of the first embodiment of the invention.

Main components that drive the second bending joint part 25 in the holding arm part 20 are schematically illustrated in FIGS. 11A and 11B. Since the wiring of the driving wire W25 is deployed and expressed on a plane for simplicity, the positions of the first internal gear 50 and the second internal gear 51 are shown so as to be shifted from each other. FIG. 11A illustrates a detachment state of the drive motor part 34, and FIG. 11B illustrates a mounting state of the drive motor part 34.

Additionally, the guide gear 25e and the coupling gear 25f are schematically illustrated in circular forms for simplicity.

As illustrated in FIG. 9, if the drive motor part 34 is detached from the driving coupling part 53, the pinion 32 does not mesh with the first internal gear 50 and the second internal gear 51. For this reason, even if the drive motor part 34 is driven, a driving force is not transmitted to the first internal gear 50 and the second internal gear 51, and the driving wire W25 is not pulled by the drive motor part 34.

In this case, as illustrated in FIG. 11A, the driving wire W25 is sequentially wound around the drive pulley 25E of the second bending joint part 25, the first internal gear 50, the pulley 55 of the reference angle maintaining part 60, and the second internal gear 51. Additionally, the driving wire W25 is fixed on the outer peripheral surfaces of the first internal gear 50 and the second internal gear 51 at positions that are not illustrated and is fixed to the drive pulley 25E via the junction part 25H on the drive pulley 25E to form a loop.

In addition, FIGS. 11A and 11B are schematic views, which are simplified. For this reason, the wiring, the winding angle, the number of times of winding, and the like in the driving wire W25 are not precisely expressed.

The reference angle maintaining part 60 is a device part for setting the rotational angle of the second bending joint part 25 to a reference angle that becomes a rotational limit and maintaining the reference angle in a state where the driving coupling part 53 that is the driving force relay part is switched to the driving force release state.

In the present embodiment, the spiral spring 70 biases a rotative force to the pulley 55 in the illustrated clockwise direction. For this reason, the pulley 55 rotates in the illustrated clockwise direction, and pulls the driving wire W25 in the illustrated counterclockwise direction. That is, the path length of the second wire part W25b between the second bending joint part 25 and the pulley 55 is reduced, and the driving wire W25 is pulled so that the path length of the first wire part W25a is increased.

Accordingly, the turning supporting plate 25G (not illustrated in FIGS. 11A and 11B, refer to FIGS. 5A and 5B) fixed to the drive pulley 25E turns around the rotating shaft 25c. In this case, the turning supporting plates 25g turn similar to the turning supporting plate 25G, and the rotating shaft 25d and the coupling gear 25f are rotated in the illustrated counterclockwise direction by the turning supporting plates 25g and 25G In this case, the coupling gear 25f rolls in the illustrated counterclockwise direction along the pitch circle of the guide gear 25e that meshes therewith.

In the second bending joint part 25, the rotatable range of the guide gear 25e is ±90°. For example, when the rotational angle of the guide gear 25e is 0°, the coupling gear 25f is aligned with the rotational axis O as indicated by a two-dot chain line in FIG. 11A. When the rotational angle of the guide gear 25e is +90°, as indicated by a solid line in FIG. 11A, the coupling gear 25f moves to a position where a line segment connecting the rotating shaft 25c with the rotating shaft 25d is orthogonal to the rotational axis O, and cannot turn in the illustrated counterclockwise direction any more.

For this reason, in the driving force release state, the coupling gear 25f is moved to a position where the rotational angle is +90° by the biasing force of the spiral spring 70. In this case, the rotational angle of the turning part 25b fixed to the coupling gear 25f is doubled due to the rotation of 90° by the rolling of the coupling gear 25f and the rotation of the rotating shaft 25d around the coupling gear 25f, and is consequently brought into a +180° rotated state.

In addition, the rotatable range can be set by suitable means. For example, in a case where the movable range of the guide gear 25e is wider than ±90°, the movable range can be restricted by providing a suitable part of the second bending joint part with a butting part that limits the movable range. Additionally, the movable range may be restricted by limiting the formation range of a gear part of the guide gear 25e.

In this way, in the driving force release state, the reference angle maintaining part 60 can specify the rotational angle of the second bending joint part 25 to +180 degrees that is a rotational limit, and can maintain this rotational angle as long as the driving force relay part is in the driving force release state.

In this case, as illustrated in FIG. 5A, the second shaft-shaped part 24 and the third shaft-shaped part 26 that are coupled together via the second bending joint part 25 are brought into a state where these shaft-shaped parts are bent by +180° and are folded toward the base end side of the holding arm part 20.

The drive unit 30 provided with such a reference angle maintaining part 60 is provided to correspond to each joint part of the holding arm part 20. For this reason, in each joint part, the rotational angle of the joint part is set to each reference angle corresponding to one rotational limit, in the driving force release state due to the action of each reference angle maintaining part 60.

For example, the reference angles of the first rotation joint part 21, the first bending joint part 23, and the second rotation joint part 27 are 0°.

The reference angle of the second bending joint part 25 is +180°.

Therefore, as illustrated in FIGS. 5A and 5B, the holding arm parts 20R and 20L have an arrangement in which, in the driving force release state, the second shaft-shaped part 24 is aligned with the rotational axis O and each fourth shaft-shaped part 28 is folded to a position parallel thereto. As a result, as illustrated in FIG. 2B, the holding arm parts 20R and 20L are brought into a state where these holding arm parts are parallel to each other in the X direction.

In a state where each joint part is held at its reference angle (hereinafter referred to as a reference state) in this way, the holding arm parts 20R and 20L are housed inside of a cylindrical region formed by extending an outer peripheral surface of the distal end part 11A. Additionally, the axial length of each holding arm part 20 in the reference state is shorter than the aligned state because a portion closer to the distal end side than the second bending joint part 25 is folded.

In this way, in the reference state, each holding arm part 20 is compactly folded on the distal end surface 11a of the distal end part 11A. For this reason, in a case where the arrangement position of the holding arm part 20 is determined by bending the bending part 11B inside the body or moving the distal end part 11A forward and backward inside the body, any interference with a treatment target part, other treatment tools, or the like does not occur easily, and workability can be improved.

Additionally, in a case where the endoscope apparatus 10 for treatment is inserted into the body through tubular members, such as the overtube, the endoscope apparatus for treatment can be smoothly inserted.

Next, the operation of the second bending joint part 25 when the drive motor part 34 is mounted will be described.

For example, as illustrated in FIG. 8, if the drive motor part 34B is mounted on the driving coupling part 53, the pinion 32 meshes with the internal-teeth parts 50b and 51b of the first internal gear 50 and the second internal gear 51. For this reason, it is possible to transmit a driving force from the pinion 32 to the first internal gear 50 and the second internal gear 51.

That is, if a driving command value is sent from the drive amount calculation unit 100 of the control unit 5, the drive motor 34A is driven, the pinion 32 rotates, and a driving force is transmitted to the first internal gear 50 and the second internal gear 51.

Although the configuration of each holding arm part 20 in the driving force release state and the driving force relay state has been described above, it is necessary to perform an initialization operation in order to perform treatment using each holding arm part 20.

In the following, a manipulator initialization method of the present embodiment for performing such an initialization operation will be described.

FIG. 12 is a flowchart illustrating the flow of the manipulator initialization method of the first embodiment of the invention.

The manipulator initialization method of the present embodiment is a method of performing Steps S1 to S5 illustrated in FIG. 12 according to the flow of FIG. 12.

First, Step S1 is performed. This step is a step of setting the rotational angle of each joint part to the reference angle and maintaining the reference angle in a state where the driving force relay part is switched to the driving force release state.

In the endoscope apparatus 10 for treatment, by bringing the drive motor part 34 into the detachment state in the drive unit 30, the driving coupling part 53 that is the driving force relay part is switched to the driving force release state, and as described above, each joint part is set to have the reference angle (reference state).

In this reference state, a biasing force resulting from the spiral spring 70 is exerted on the driving wire that drives each joint part, and is maintained until an external force exceeding this biasing force is exerted. Additionally, even if the external force is temporarily exerted and each joint part deviates from the reference state, the reference state is reproduced due to the elastic restoring force of the spiral spring 70 if the external force disappears.

In the present embodiment, this step is performed before the distal end part 11A including each holding arm part 20 of the endoscope apparatus 10 for treatment is inserted into the body of the patient P. However, in a case where the distal end part can be inserted into the body even in the driving force relay state, it is also possible to perform the insertion after the distal end part is moved to the inside of the body. Additionally, in a case where each holding arm part 20 already moved to the inside of the body is initialized again, this step is performed inside the body.

Next, Step S2 is performed. This step is a step of inserting each joint part into the body in the driving force release state.

That is, each holding arm part 20 in the driving force release state is inserted into the body of the patient P from the distal end part 11A by bringing the drive motor part 34 into the detachment state. For this reason, each holding arm part 20 is inserted into the body in the reference state.

The above completes Step S2.

In addition, this step is skipped in a case where Step S1 is performed inside the body of the patient P.

Next, Step S3 is performed. This step is a step of switching the driving force relay part to the driving force relay state, in a state where each joint part is arranged inside the body that is a position where the initialization operation is performed after Step S1 is performed that is a reference angle maintaining step, and constitutes a drive part coupling step.

In the present embodiment, specifically, the distal end part 11A is positioned in a suitable treatment region and the drive motor part 34 is mounted, after the above Step S2 is performed and the distal end part 11A including each holding arm part 20 is inserted into the body of the patient P. In addition, in a case where Step S2 is skipped after the distal end part 11A is inserted into the body in Step S1, in this step, the distal end part 11A is moved to a suitable treatment region if necessary and the drive motor part 34 is mounted.

In this way, if the drive motor part 34 is mounted, each driving coupling part 53 is brought into the driving force relay state.

The above completes Step S3.

Next, Step S4 is performed. This step is a step of matching the driving origin of each drive part according to the state of the rotational angle of each joint part after each joint part is rotated by a predetermined angle from the reference angle, and constitutes an origin setting step.

When the drive motor part 34 is mounted, the driving coupling part 53 is brought into the drive amount relay state, and it is possible to drive each joint part on the basis of a driving command value that the drive amount calculation unit 100 calculates.

The origin setting unit 101 sends a control signal for causing the drive amount calculation unit 100 to calculate a driving command value corresponding to the amount of driving that rotates each joint part by a predetermined angle, for example, if the origin setting unit is notified of being changed into the driving force relay state by the notification means (not illustrated), such as a detection sensor.

The predetermined angle is a difference between the rotational angle and the reference angle of each joint part that realizes the orientation in the origin of the holding arm part 20.

In the present embodiment, as an example, the aligned state is adopted as the origin orientation. For this reason, the predetermined angle is 0° with respect to the first rotation joint part 21, the first bending joint part 23, and the second rotation joint part 27. In the second bending joint part 25, the angle of −90° is determined in advance with respect to the reference angle of +180°.

The drive amount calculation unit 100 calculates the driving command values based on these angles, each driving command value is sent to each joint part, the drive motor part 34 that drives each joint part is driven, and a driving force is transmitted to each joint part via each driving wire. Since this driving force has a magnitude exceeding the biasing force of the spiral spring 70, the driving wire is pulled according to the rotational amount and the rotational direction of the pinion 32 of the drive motor part 34.

Accordingly, the second bending joint part 25 rotates by −90°, and the rotational angle of the second bending joint part 25 reaches 0°. As a result, each holding arm part 20 is brought into the aligned state as illustrated in FIG. 4.

Next, the drive amount calculation unit 100 matches and stores the rotational angle of each joint part in this state with the driving origin of the drive motor part 34. Accordingly, the drive amount calculation unit 100 calculates the amount of driving by recognizing the rotational position of each current drive motor 34A as the drive origin.

The above completes Step S4.

Accordingly, the operation input of the master arm 3 and the operation of each holding arm part 20 come to correspond to each other precisely. Additionally, the aligned state is reproduced if an operation input of returning the orientation of the holding arm part 20 to the origin orientation is performed from the master arm 3.

Next, Step S5 is performed. This step is a step of setting the drive limit from the drive origin when each joint part is driven, and constitutes a drive limit setting step.

After the origin of the driving command value is set in the above Step S4, the origin setting unit 101 sends a driving command value corresponding to the drive limit, which is determined in advance with respect to each joint part, to the drive amount calculation unit 100, and stores the driving command value in the drive amount calculation unit 100.

For example, even in a case where the movable range of a specific joint part is ±x0 from the origin at the driving command value, an operationally required driving range of the holding arm part 20 is only ±x (where, x<x0) in many cases. If the joint part is allowed to move beyond this movable range, the joint part may interfere with other treatment tools or instruments inside the body of the patient P in a case where an operation is excessively and erroneously performed. Additionally, the load applied to each driving wire may become excessive, and the driving wire and the manipulator may be damaged.

For this reason, in the present embodiment, for example, the above driving command value x is stored as the drive limit in the drive amount calculation unit 100.

The above completes Step S5, and the manipulator system initialization method of the present embodiment with respect to each holding arm part 20 is completed.

After the initialization of the holding arm part 20 is completed in this way, it is possible for the operator Op to start suitable treatment.

The operator Op performs a predetermined operation input for operating the master arm 3 to bend the holding arm part 20 or grasping a treatment site or the like with the grasping part 29, according to the necessity of a treatment operation, while viewing an image of a surgical field by the display unit 4.

For example, if the operation input of bending the holding arm part 20 is performed, the drive amount calculation unit 100 of the control unit 5 analyzes the operation input of the master arm 3 to obtain the joint angle of each joint part that realizes a bent state that is input for operation, and calculates a driving command value with respect to each drive motor 34A that transmits a driving force to each joint part, according to each joint angle.

The drive amount calculation unit 100 determines whether or not each driving command value exceeds the drive limit, and sends each driving command value to each drive motor part 34 in a case where all driving command values are within a range of the drive limit.

In a case where a driving command value exceeding the drive limit is present, the drive amount calculation unit 100 stops the sending of each driving command value, and causes the display unit 4 to display a message warning that the driving command value exceeds the drive limit. The operator Op views the message of the display unit 4, and changes the operation input of the master arm 3.

If the driving command value is sent to each drive motor part 34, the pinion 32 of each drive motor part 34 rotates, each driving wire is pulled, and each joint part is driven. In this way, the holding arm part 20 is bent on the basis of the operation of the master arm 3.

In inserting the overtube 11 into the body of the patient P and moving the distal end part 11A to the treatment region, the insertion part 11C having flexibility is bent. For this reason, each sheath inserted into the insertion part 11C and each driving wire inserted through this sheath are bent, and the path length of the driving wire varies in a straight state. In a case where origin seek of the holding arm part 20 is performed in a state different from such a bent state, there is a concern that an origin position may shift inside the body, which becomes a hindrance to operation.

However, in the present embodiment, since a state where a given amount of driving is performed from the reference state inside the body is matched with the driving origin of the drive motor part 34, the origin position can be initialized without being influenced by the bent state of the sheath and the driving wire. For this reason, precise driving can be performed inside the body.

In contrast, it is also conceivable that the origin orientation of the holding arm part 20 is defined by a dedicated jig and the like and matching with the driving origin is performed. However, in the present embodiment, the reference state of the holding arm part 20 can be formed without using such a dedicated jig. Therefore, the initialization operation can be easily performed even inside the body.

In this way, according to the present embodiment, the origin setting can be performed by switching the driving force relay part to the driving force relay state after the rotational angle of each joint part is set to the reference angle. Therefore, the initialization of matching the rotational angle of the joint part with the origin position of each motor can be easily performed even after insertion into the body.

(First to Third Modification Examples) Next, manipulators of modification examples (first to third modification examples) of the above first embodiment will be described. All of the first to third modification examples are modification examples regarding the arrangement position of the reference angle maintaining part.

Figure 13A:
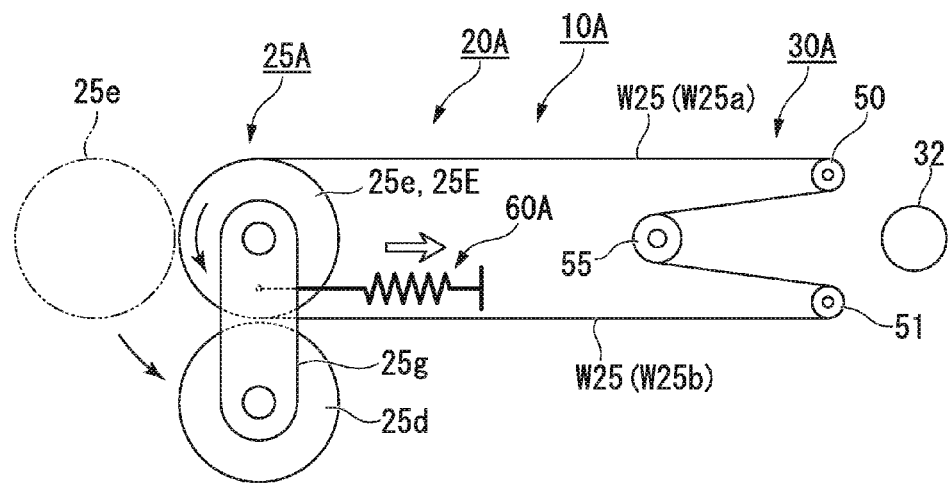
FIG. 13A is a schematic view illustrating the configuration of a driving force release state of principal parts of a manipulator of a modification example (first modification example) of the first embodiment of the invention.
Figure 13B:
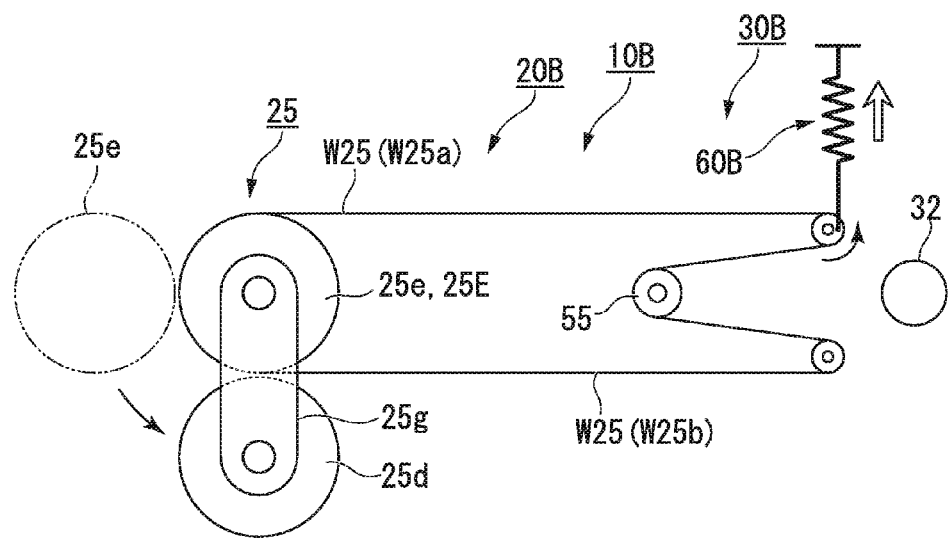
FIG. 13B is a schematic view illustrating the configuration of a driving force release state of principal parts of a manipulator of a modification example (second modification example) of the first embodiment of the invention.
Figure 13C:
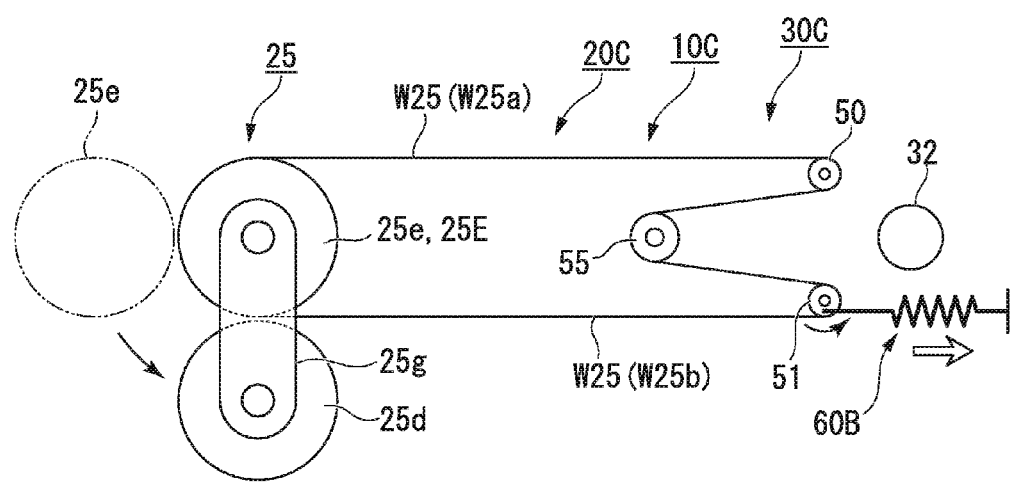
FIG. 13C is a schematic view illustrating the configuration of a driving force release state of principal parts of a manipulator of a modification example (third modification example) of the first embodiment of the invention.

FIGS. 13A, 13B, and 13C are schematic views illustrating the configuration of the driving force release state of principal parts of the manipulators of the modification examples (first to third modification examples) of the first embodiment of the invention.

As illustrated in FIG. 1, a manipulator system 1A of the first modification example includes an endoscope apparatus 10A (manipulator) for treatment, instead of the endoscope apparatus 10 for treatment of the manipulator system 1 in the above first embodiment.

As illustrated in FIG. 13A, the endoscope apparatus 10A for treatment includes a holding arm part 20A (medical instrument) and a drive unit 30A, instead of the holding arm part 20 and the drive unit 30 in the above first embodiment.

Hereinafter, differences from the above first embodiment will mainly be described.

In the holding arm part 20A, the reference angle maintaining part is configured to apply a biasing force to a rotating body within each joint part that drives the joint part. For example, the second bending joint part 25A has a reference angle maintaining part 60A, which generates a biasing force for rotating the drive pulley 25E in the illustrated counterclockwise direction, to the support part 25a (not illustrated).

As for the reference angle maintaining part 60A, for example, a configuration using the same spiral spring 70 as that of the above first embodiment is possible. However, the reference angle maintaining part 60A is not limited to the spiral spring 70 if the biasing force for rotating the drive pulley 25E or the turning supporting plate 25G in one direction, can be generated. For example, a tension spring, a constant force spring, a pneumatic spring, and a mechanism that generates a biasing force using magnetism are also possible.

In addition, FIG. 13A illustrates a conceptual configuration for a schematic view (the same applies to FIGS. 13B and 13C). For this reason, although it is illustrated as if the drive pulley 25E is directly tensioned by the tension spring, the invention is not limited to such a form.

For example, a configuration in which a wire member for tension is wound around the drive pulley 25E by a suitable amount, and this wire member is connected to a tension spring and the like so as to generate the biasing force for rotating the drive pulley 25E is possible.

The drive unit 30A is obtained by eliminating the reference angle maintaining part 60 from the drive unit 30 in the above first embodiment.

According to the endoscope apparatus 10A for treatment, in the driving force release state, for example, the drive pulley 25E is rotated to a position that reaches the reference angle by the biasing force generated in the reference angle maintaining part 60A, and this also applies to the other joint parts. Therefore, the holding arm part 20A is in the reference state.

According to such an endoscope apparatus 10A for treatment, the initialization operation can be performed similar to the above first embodiment.

As illustrated in FIG. 1, a manipulator system 1B of the second modification example includes an endoscope apparatus 10B (manipulator) for treatment, instead of the endoscope apparatus 10 for treatment of the manipulator system 1 in the above first embodiment.

As illustrated in FIG. 13B, the endoscope apparatus 10B for treatment includes a drive unit 30B, instead of the drive unit 30 in the above first embodiment.

Hereinafter, differences from the above first embodiment will mainly be described.

In the drive unit 30B, the reference angle maintaining part 60 of the drive unit 30 is eliminated, and a reference angle maintaining part 60B that generates a biasing force for rotating the first internal gear 50 (the rotating body that drives each joint part) in one direction is provided.

For example, the drive unit 30B corresponding to the second bending joint part 25 includes the reference angle maintaining part 60B that generates the biasing force for rotating the first internal gear 50 in the illustrated counterclockwise direction.

As for the reference angle maintaining part 60B, for example, the configuration using the same spiral spring 70 as that of the above first embodiment is possible. However, the reference angle maintaining part 60B is not limited to the spiral spring 70 if the biasing force for rotating the first internal gear 50 in one direction can be generated. For example, a tension spring, a constant force spring, a pneumatic spring, and a mechanism that generates a biasing force using magnetism are also possible.

According to the endoscope apparatus 10B for treatment, in the driving force release state, the first internal gear 50 within the drive unit 30D is rotated in one direction by the biasing force generated in the reference angle maintaining part 60B. As a result, for example, the drive pulley 25E is rotated to a position that reaches the reference angle, and this also applies to the other joint parts. Therefore, the holding arm part 20B is brought into the reference state.

According to such an endoscope apparatus 10B for treatment, the initialization operation can be performed similar to the above first embodiment.

As illustrated in FIG. 1, a manipulator system 1C of the third modification example includes an endoscope apparatus 10C (manipulator) for treatment, instead of the endoscope apparatus 10 for treatment of the manipulator system 1 in the above first embodiment.

As illustrated in FIG. 13C, the endoscope apparatus 10C for treatment includes a drive unit 30C, instead of the drive unit 30 in the above first embodiment.

Hereinafter, differences from those of the above first embodiment and the above second modification example will mainly be described.

The drive unit 30C is a modification example in which the reference angle maintaining part 60B provided for the first internal gear 50 in the drive unit 30B of the above second modification example is provided for the second internal gear 51 (a rotating body that drives each joint part).

According to the present modification example, there is a difference only in that the reference angle maintaining part 60B is provided in the second internal gear 51, instead of the first internal gear 50. Therefore, the same effects as those of the above second modification example are provided.

Second Embodiment

Next, a manipulator of a second embodiment of the invention will be described.

Figure 14:
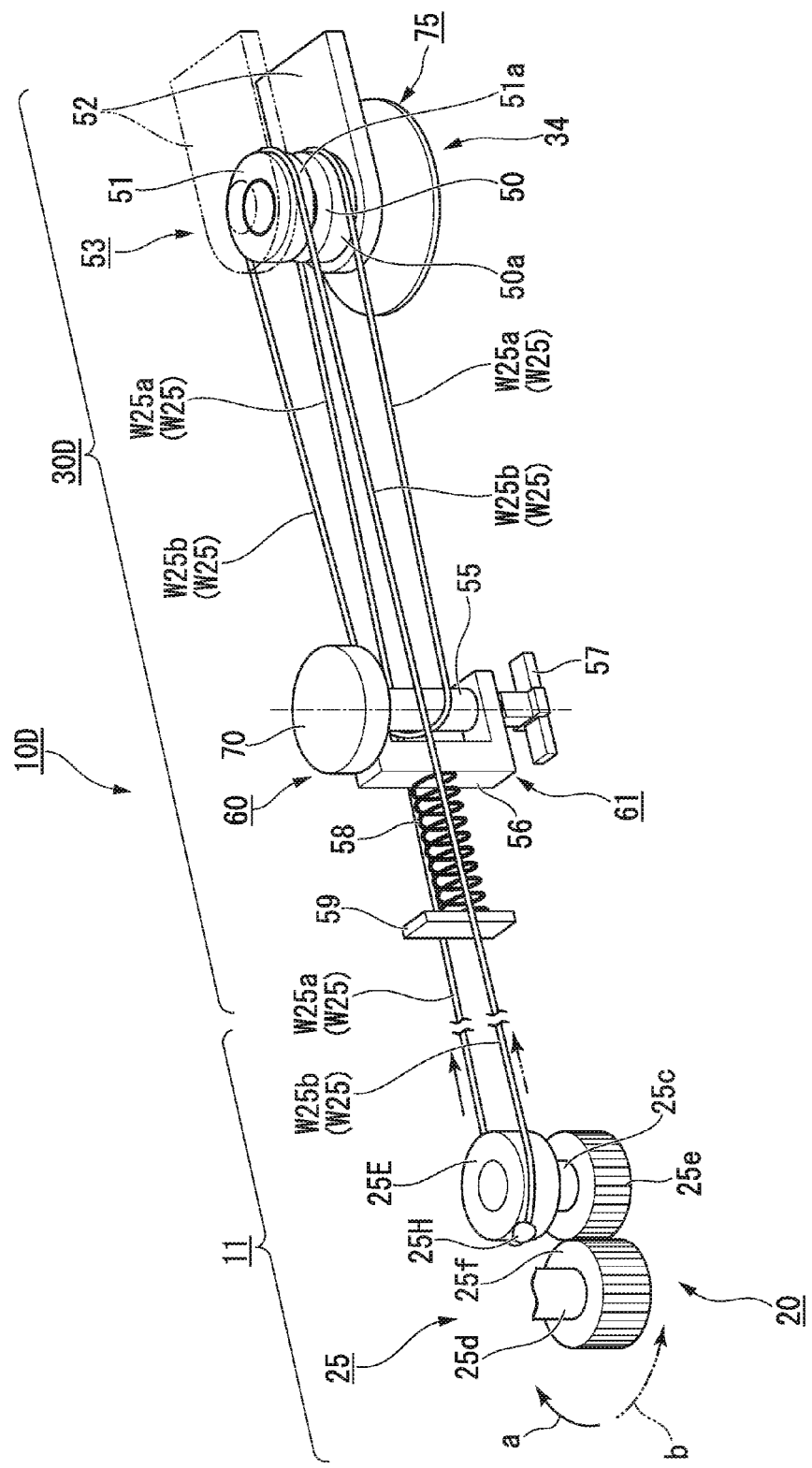
FIG. 14 is a schematic perspective view illustrating the configuration of a reference angle maintaining part and an initial tension application part of a manipulator of a second embodiment of the invention.

FIG. 14 is a schematic perspective view illustrating the configuration of a reference angle maintaining part and an initial tension application part of the manipulator of the second embodiment of the invention.

As illustrated in FIG. 1, a manipulator system 1D of the present embodiment includes an endoscope apparatus 10D (manipulator) for treatment, instead of the endoscope apparatus 10 for treatment of the manipulator system 1 in the above first embodiment.

As illustrated in FIG. 14, the endoscope apparatus 10D for treatment includes a drive unit 30D, instead of the drive unit 30 in the above first embodiment.

Hereinafter, differences from the above first embodiment will mainly be described.

As illustrated in FIG. 14, the drive unit 30D is obtained by adding an initial tension application part 61 to the above first embodiment.

The initial tension application part 61 includes a guide 57 that slidably holds the pulley holding part 56 of the reference angle maintaining part 60 in a direction in which a distal end (a left side in the illustration of FIG. 14) and a proximal end (a right side in the illustration of FIG. 14) are connected together, a spring 58 disposed on the distal side of the pulley holding part 56 to pull the pulley holding part 56 toward the distal end side, and a support part 59 that supports a distal end of the spring 58.

The guide 57 and the support part 59 are fixed to the housing part 31 (not illustrated in FIG. 14, refer to FIG. 1).

For this reason, the spring 58 tensions the pulley holding part 56 and the spiral spring 70 fixed thereto 56 to the distal end side along the guide 57. Accordingly, an initial tension corresponding to the elastic restoring force of the spring 58 is applied to the driving wire W25. In this case, since the pulley holding part 56 is pulled by the spring 58 and is moved on a straight line, a configuration in which the guide 57 is eliminated is also possible.

However, the spring 58 may be arranged so as to press the pulley holding part 56 toward the distal end side. In this case, since there is a concern that the spring 58 may be buckled to the lateral side of an expansion/contraction direction thereof, the spring 58 may have a configuration that is different from the guide 57. However, it is preferable to provide a certain movement guide part that defines the movement direction of the pulley holding part 56.

In the present embodiment, it is preferable to set the magnitude of the force of the spiral spring 70 of the reference angle maintaining part 60 and the magnitude of the force of the spring 58 of the initial tension application part 61 such that the driving force for driving each joint part does not become too large.

Particularly the biasing force of the reference angle maintaining part 60 becomes driving resistance in a case where each joint part is driven in a direction opposite to the biasing force resulting from the spiral spring 70. For this reason, since a required driving force varies depending on driving directions, it is preferable that the biasing force of the spiral spring 70 be as small as possible. Therefore, it is preferable to set the spring characteristics of the spiral spring 70 and the spring 58 so that a tension component of the driving wire W25 resulting from a force biased by the spiral spring 70 becomes sufficiently smaller than an initial tension component applied by the spring 58.

Next, the operation of the drive unit 30D will be described with a central focus on the operation of the endoscope apparatus 10D for treatment.

Figure 15A:
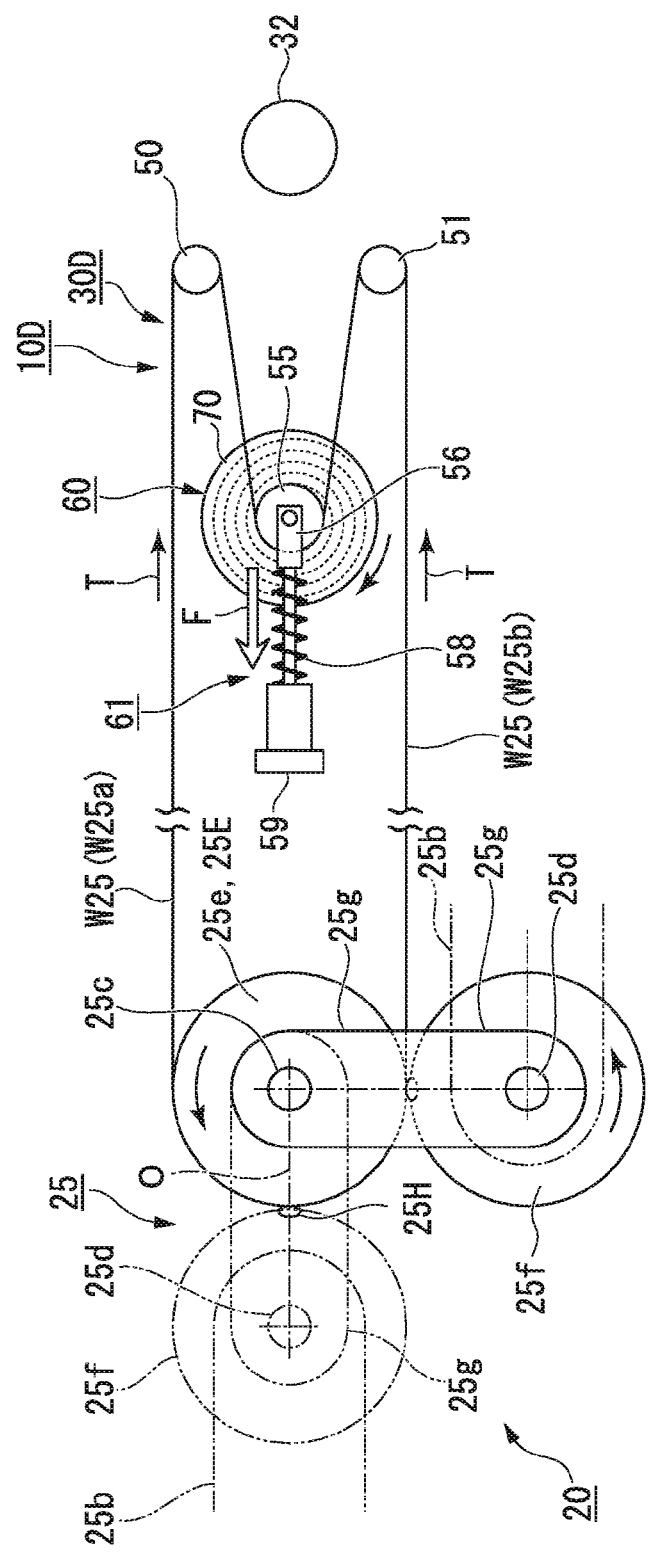
FIG. 15A is a schematic explanatory view of the operation of the manipulator of the second embodiment of the invention.
Figure 15B:
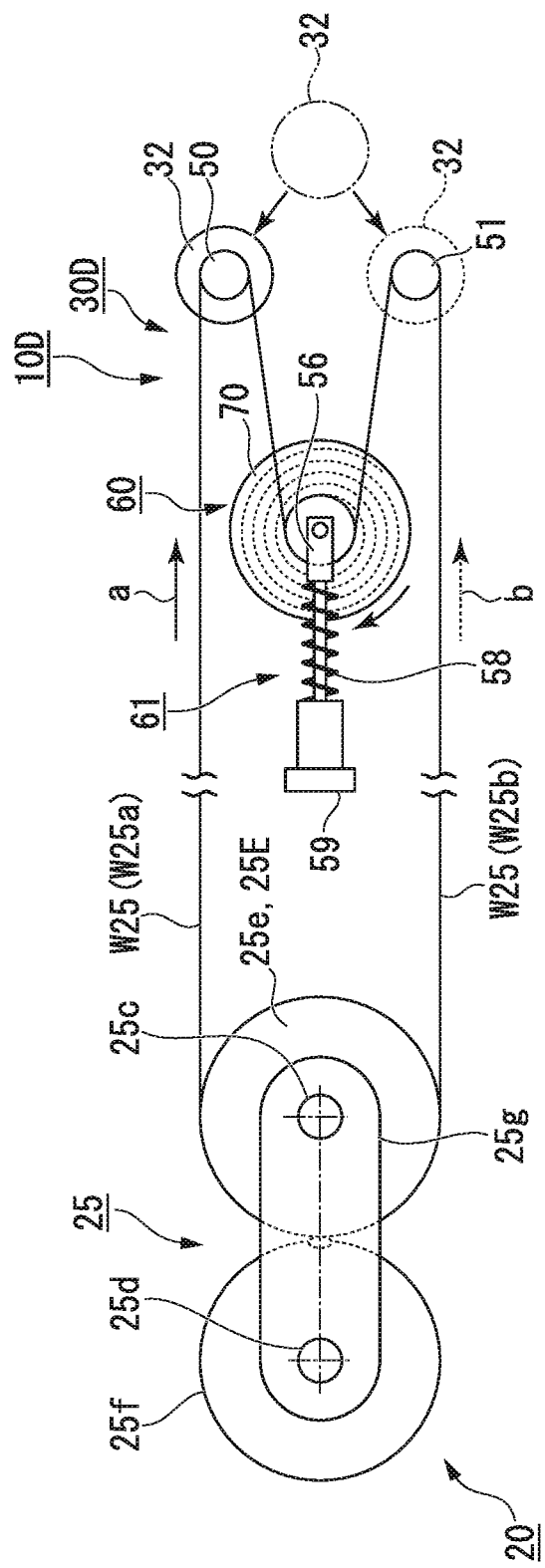
FIG. 15B is a schematic explanatory view of the operation of the manipulator of the second embodiment of the invention.

FIGS. 15A and 15B are schematic explanatory views of the operation of the manipulator of the second embodiment of the invention. FIG. 16 is a flowchart illustrating the flow of a manipulator initialization method of the second embodiment of the invention.

Main components that drive the second bending joint part 25 in the holding arm part 20 are schematically illustrated in FIGS. 15A and 15B, similar to FIGS. 11A and 11B. FIG. 15A illustrates the detachment state of the drive motor part 34, and FIG. 15B illustrates the mounting state of the drive motor part 34. Therefore, FIG. 15A illustrates the driving force release state of the driving coupling part 53, and FIG. 15B shows the driving force relay state of the driving coupling part 53.

In the present embodiment, the pulley 55 is pulled to the distal end side with a force F by the spring 58 of the initial tension application part 61. For this reason, in each of the first wire part W25a and the second wire part W25b divided with the pulley 55 as a border, an initial tension T (=F/2) is applied to the driving wire W25.

Accordingly, the driving wire W25 is stretched without causing loosening.

In this state, since a biasing force in the illustrated clockwise direction is applied to the pulley 55 by the spiral spring 70 of the reference angle maintaining part 60, the coupling gear 25f turns to a position where the second bending joint part 25 reaches +180° that is the reference angle.

Since the pulley 55 is movable along the guide 57, the pulley 55 comes to rest at a position where an elastic restoring force exerted from the spring 58 and the spiral spring 70, the tension of the driving wire W25, and a frictional force from the driving wire W25 are balanced with each other. That is, if the driving wire W25 is loosened, the spring 58 is contracted and the loosening thereof is always removed, and the tension of the driving wire W25 becomes uniform.

In this way, in the driving force release state, the pulley 55 coupled to the spiral spring 70 constitute the rotating body for driving the driving wire W25.

If the drive motor part 34 is mounted, and the driving of the second bending joint part 25 is started as the driving force relay state, the same operation as that of the above first embodiment is performed. However, since the present embodiment includes the initial tension application part 61, the pulley 55 is always pulled to the distal end side, and the loosening of the driving wire W25 that serves as a loosening side at the time of driving is removed.

By virtue of such a configuration, the holding arm part 20 can be initialized substantially similar to that of the above first embodiment.

The manipulator initialization method of the present embodiment is a method of performing Steps S11 to S16 illustrated in FIG. 16 according to the flow of FIG. 16.

First, Step S11 is performed. This step is a step of applying the initial tension to the driving force transmission member in order to remove loosening of the driving force transmission member, and constitutes an initial tension applying step.

In the endoscope apparatus 10D for treatment, the drive unit 30D has the initial tension application part 61. Therefore, the initial tension T is always applied to the driving wire that is the linear driving force transmission member, for example, the driving wire W25 or the like.

For this reason, this step is not a step where the operator Op and the control unit 5 need to perform particularly a certain operation.

Next, Steps S12 to S16 are performed. Steps S12 to S16 are the same steps as Steps S1 to S5 (refer to FIG. 12) of the above first embodiment except that the holding arm part 20 in the endoscope apparatus 10D for treatment is initialized.

However, in the present embodiment, the endoscope apparatus 10D for treatment has the reference angle maintaining part 60, and thereby, the reference angle is always maintained in the driving force release state. Therefore, Step S11 and Step S12 do not necessarily have an anteroposterior relationship clearly, and Step S11 and Step S12 are simultaneously performed when the driving force release state is brought about.

After the initialization of the holding arm part 20 is completed in this way, it is possible for the operator Op to start suitable treatment, similar to the above first embodiment.

In the present embodiment, the initial tension application part 61 is provided, and thereby, the loosening of the driving force transmission member is reliably removed when switching to the driving force relay state is performed. Therefore, the matching with the driving origin in Step S15 can be precisely performed without an error.

Particularly, since the loosening caused by a change in path length generated by the bent state of the sheath and the driving wire is also reliably removed, the initialization precision of the origin position can be improved. For this reason, more precise driving can be performed inside the body.

In this way, according to the present embodiment, the origin setting can be performed by switching the driving force relay part to the driving force relay state after the rotational angle of each joint part is set to the reference angle. Therefore, even after insertion into the body, the initialization of matching the rotational angle of the joint part with the origin position of each motor can be easily performed.

Third Embodiment

Next, a manipulator of a third embodiment of the invention will be described.

Figure 17:
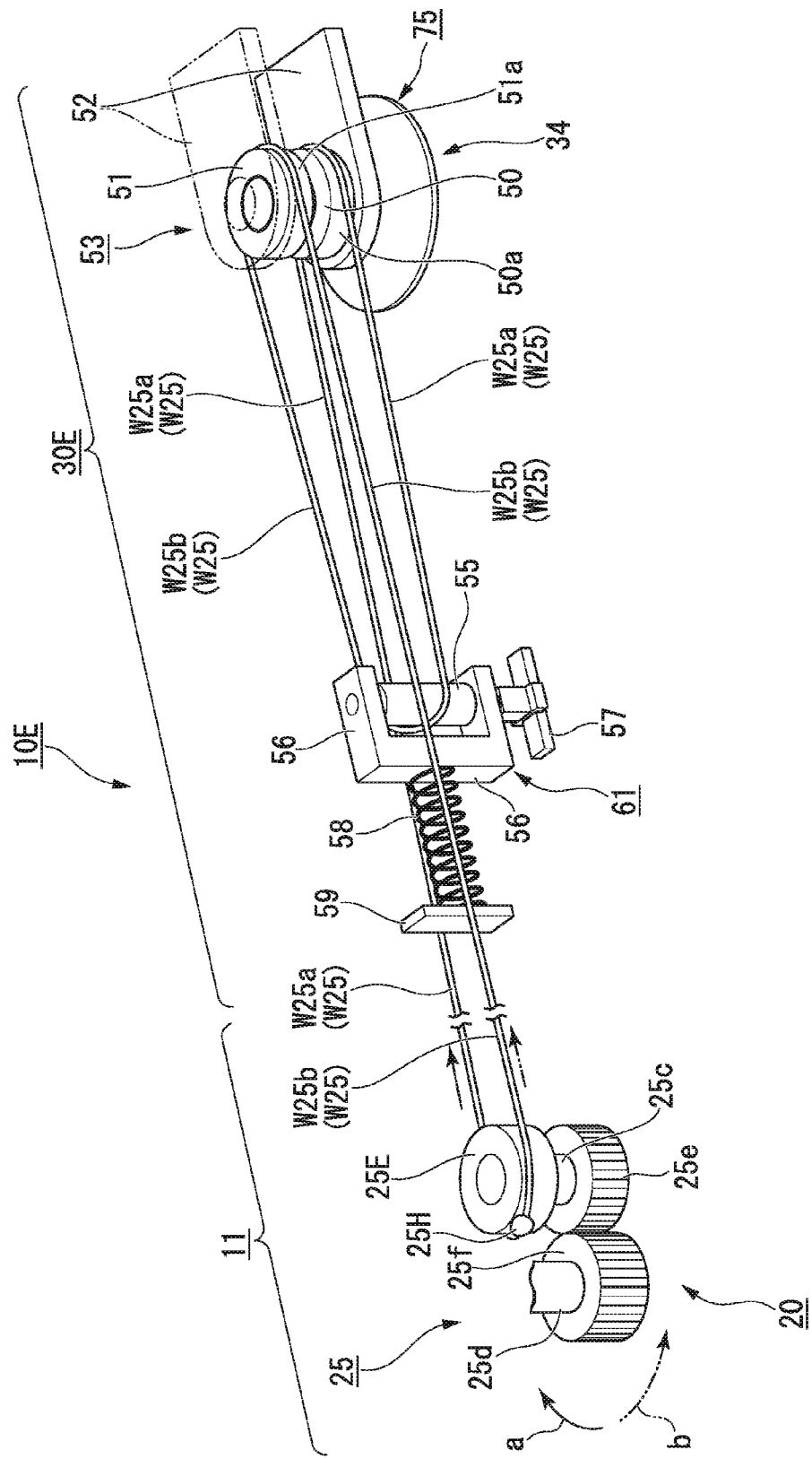
FIG. 17 is a schematic perspective view illustrating the configuration of an initial tension application part of a manipulator of a third embodiment of the invention.

FIG. 17 is a schematic perspective view illustrating the configuration of an initial tension application part of a manipulator of the third embodiment of the invention.

As illustrated in FIG. 1, a manipulator system 1E of the present embodiment includes an endoscope apparatus 10E (manipulator) for treatment, instead of the endoscope apparatus 10 for treatment of the manipulator system 1 in the above first embodiment.

As illustrated in FIG. 17, the endoscope apparatus 10E for treatment includes a drive unit 30E, instead of the drive unit 30 in the above first embodiment.

The drive unit 30E is obtained by eliminating the spiral spring 70 of the reference angle maintaining part 60 from the drive unit 30D in the above second embodiment. For this reason, the pulley holding part 56 does not have the functions as the reference angle maintaining part, and has only some functions of the initial tension application part 61. For this reason, the present embodiment is an example in a case where the reference angle maintaining part is eliminated from the above second embodiment.

Hereinafter, differences from those of the above first and second embodiments will mainly be described.

According to such an endoscope apparatus 10E for treatment, the holding arm part 20 can be initialized by performing Steps S11 to S16 illustrated in FIG. 16, substantially similar to the above second embodiment.

Step S11 of the present embodiment is the same step as Step S11 of the above second embodiment except that this step is point performed using the endoscope apparatus 10E for treatment.

Next, Step S12 of the present embodiment is performed. Since the endoscope apparatus 10E for treatment does not have the reference angle maintaining part 60, the initial tension is applied to each driving wire when Step S11 is completed. However, since the initial tension is balanced, the rotational angle of each joint part is unfixed. For this reason, the reference state is not necessarily formed.

In the present embodiment, in such a driving force release state, each joint part of the holding arm part 20 can be easily moved if an external force is exerted. Thus, in this step, the reference state is formed by exerting an external force on the holding arm part 20.

Specifically, it is possible to manually rotate and fold each joint to its rotational limit.

Additionally, it is possible to position the reference state by fitting each joint in a jig having a hole capable of fitting in the reference state while manually folding each joint. However, the jig is detached if the reference state is formed.

In this way, if the reference state is formed in this way, the reference state is maintained by a frictional force between the driving wire and the rotating body around which the driving wire is wound. Since the frictional force also becomes large according to the magnitude of the initial tension if the initial tension is applied, it is easy to maintain the reference state.

The above completes Step S12 of the present embodiment.

Next, Steps S13 to S16 of the above second embodiment are performed in a similar way.

However, in Step S13, insertion into the body is carefully performed so that an external force to change the reference state is not exerted.

In this way, each holding arm part 20 of the endoscope apparatus 10E for treatment is initialized.

In addition, in the description of the above respective embodiments and the above respective modification examples, an example in a case where the grasping part 29 that is grasping forceps is provided has been described as an end effector of a medical instrument. However, the end effector is not limited to the grasping part 29, and a suitable device configuration, for example, a high-frequency treatment tool, a local injection needle, peeling forceps, suction, and the like are possible according to the type of procedure. Additionally, the end effector is not limited to a movable mechanism like the grasping part 29, either. For example, an end effector of being only fixed to the distal end like the observation unit 15 of the endoscope apparatus 10 for treatment may be adopted.

In the description of the above respective embodiments and the above respective modification examples, examples in cases where the manipulator initialization methods are initialization methods of medical manipulators have been described. However, the invention can also be similarly applied to manipulators other than the medical manipulators, for example, industrial manipulators and industrial manipulator systems. In this case, the medical instrument having the joint parts that rotate the objects to be rotated can be replaced with instruments having joint parts that rotate objects to be rotated, industrial instruments, or industrial treatment tools.

In the description of the above respective embodiments and the above respective modification examples, an example in a case where the holding arm part 20 has the two rotation joints and the two bending joints as the joint parts has been described. However, this is merely an example, and the number and degree of freedom of joint parts can be appropriately set in consideration of the contents of a procedure, or the like. Additionally, the same mechanism as the bending part 11B in the overtube 11 may be used instead of the combination of the joint parts and the shaft-shaped parts.

That is, the objects to be rotated by the joint parts are not limited to the shaft-shaped parts, and may be annular members like a plurality of joint rings or bending pieces, and objects to be rotated with forms that do not have clear axes can also be used.

In the description of the above respective embodiments and the above respective modification examples, an example in a case where the drive limit is set only by the soft setting of limiting the driving command value of the drive motor 34A has been described. However, for example, as the drive motor 34A, it is possible to adopt a drive part having a position sensor that can detect a position reaching an allowable limit of the rotational angle to perform the origin seek of the drive motor 34A. As the position sensor, for example, sensors such as an optical sensor and a mechanical sensor can be adopted.

In this case, in the origin setting step, it is preferable to perform an origin seeking step of performing the origin seek of the drive part, on the basis of a detection output of the position sensor until the driving force relay part is switched to the driving force relay state.

In this step, for example, the origin seek such that the rotational angle of the drive part is changed to the center position of the position reaching the allowable limit by the position sensor is performed.

In this case, in a case where priority is given to the drive limit based on the position sensor, a substantial driving range can be prevented from being limited. Additionally, in a case where priority is given to the drive limit of the soft setting, the drive limit can be prevented from being set beyond the drive limit based on the position detecting sensor.

In the description of the above respective embodiments and the above respective modification examples, an example in a case where the drive limit setting step is performed after the origin setting step has been described. However, in a case where the drive limit does not need to be provided, it is possible not to perform the drive limit setting step.

In the description of the above respective embodiments and the above respective modification examples, an example in the case of the holding arm part 20 in which the medical instrument is fixed to the distal end surface 11a of the distal end part 11A of the overtube 11 has been described. However, the medical instrument is not limited to this.

For example, a configuration in which a shaft-shaped medical instrument that can move an end effector by means of a multi joint structure is inserted through a treatment tool channel, a guide tube, a trocar, or the like of an endoscope and inserted into a body is also possible.

In the description of the above respective embodiments and the above respective modification examples, an example in a case where a medical instrument is a flexible treatment tool has been described. However, the medical instrument can also be a rigid treatment tool if the joint parts that rotate the objects to be rotated are provided.

In the description of the above respective embodiments and the above respective modification examples, an example in a case where the driving force relay part attaches and detaches the drive part has been described. However, it is not indispensable to attach and detach the drive part.

For example, a configuration in which the drive part and the driving force transmission part are coupled together by a clutch is possible. In this case, the driving force relay state is formed by interlocking the drive part with the driving force transmission part with the clutch, and the driving force release state is formed by releasing the interlocking between the drive part and the driving force transmission part with the clutch, thereby cutting off the driving force.

For example, in the case of the drive part and the driving force transmission part that drive the driving wire W25 of the above first embodiment, two driving force transmission parts equivalent to the first internal gear 50 and the second internal gear 51 rotate integrally with the drive part equivalent to the drive motor part 34 in the driving force relay state, and the driving force resulting from the drive part needs to be cut off in the driving force release state. Moreover, in the driving force release state, it is necessary to allow two drive parts to rotate independently from each other in order to solve loosening.

An example of such a configuration will simply be described.

As the driving force transmission parts, two pulleys, which include outer peripheral surfaces 50a and 51a, are supported so as to be capable of being brought close to and separated from each other in directions along their rotational axes, and are integrally rotated at the time of abutment by mating surfaces formed in concave-convex surfaces or the like being adopted instead of the first internal gear 50 and the second internal gear 51.

Additionally, as the drive part, a drive motor part, which is capable of pressing these pulleys along the rotational axes and is provided with an engagement plate that rotates integrally with the pulleys at the time of pressing, is adopted instead of the pinion 32 of the drive motor part 34.

As the clutch, a mechanism which moves the drive motor part forward and backward in a rotational axis direction between a first position where the engagement plate is separated from the pulleys and a second position where the engagement plate is pressed toward the pulleys until the two pulleys are integrated with each other is adopted.

According to such a configuration, if the drive motor part is moved to the first position by the clutch, the driving force release state is brought about. In this case, since the two pulleys are separated from each other, these pulleys can be rotated freely from each other.

If the drive motor part is moved to the second position by the clutch, the engagement plate presses the two pulleys, and the engagement plate and the two pulleys are coupled together in the rotational axis direction.

For this reason, if the drive motor part rotates, a driving force from the drive motor part is relayed, and the two pulleys rotate in synchronization with each other. That is, the driving force relay state is formed.

In the configuration in which such a clutch is provided, the above notification means can be configured by sending a control signal for turning the clutch on and off, or a signal indicating an on/off state of the clutch to the origin setting unit 101.

In the description of the above first and second embodiments, an example in a case where a biasing force is applied to a rotating body that drives each joint part has been described as the reference angle maintaining part. However, the reference angle maintaining part is not limited to this.

For example, a configuration in which the objects to be rotated by the joint parts are pressed in the rotational direction and the reference angles are set, and mechanisms or members that restrict the positions of the objects to be rotated described in the third embodiment to set the reference angles can be adopted.

For example, a configuration in which the objects to be rotated are pressed by members to be dissolved inside the body or the positions thereof are restricted, so that the pressing and the position restriction can be released inside the body is possible.

Additionally, it is possible to adopt a configuration in which a shape-memory alloy performs switching between a state where, according to temperature, the objects to be rotated are pressed or the positions thereof are restricted or a state where the pressing and the position restriction are released. In this case, it is possible to form the reference state at a temperature outside a body and to release the restriction of the reference state at a temperature inside the body.

All the constituent elements described in the above may be carried out by appropriate combination or elimination in the scope of the technical idea of the invention.

For example, all of the first to third modification examples of the above first embodiment can also be applied to the endoscope apparatus 10D for treatment of the second embodiment and the endoscope apparatus 10E for treatment of the third embodiment.

What is claimed is:
1. An initialization method for a manipulator,
wherein the manipulator includes:
a medical instrument having a joint that rotates an object to be rotated;
a driving force transmission that transmits a driving force to the joint;
an actuator that supplies the driving force to the driving force transmission; and
a coupling capable of being switched between a driving force relay state where the driving force is relayed and a driving force release state where the driving force is cut off,
the initialization method comprising:
setting a rotational angle of the joint to a reference angle that has been predetermined, and maintaining the reference angle in a state where the coupling is switched to the driving force release state;
subsequent to setting the rotational angle of the joint, switching the coupling to the driving force relay state to arrange the joint at a position where an initialization operation is performed;
rotating the joint from the reference angle by a predetermined angle to align the joint at an origin orientation different from an orientation at the reference angle, wherein the actuator rotates to a drive origin as the joint rotates from the reference angle; and
setting a rotational position of the actuator based on the rotation of the actuator to the drive origin.

2. The initialization method according to claim 1, wherein the reference angle includes an upper limit and a lower limit in which the rotational angle of the joint can be set.

3. The initialization method according to claim 1, further comprising:
rotating the joint to the predetermined angle from the reference angle before setting the rotational position of the actuator.

4. The initialization method according to claim 1, wherein setting the rotational position of the actuator includes:
setting a drive limit from the drive origin when the joint is driven with respect to the actuator.

5. The initialization method according to claim 1,
wherein the driving force transmission includes a linear driving force transmission member, and
the initialization method further comprises:
applying an initial tension to the driving force transmission member in order to remove loosening of the driving force transmission member before rotating the joint from the reference angle by the predetermined angle.

6. The initialization method according to claim 1,
wherein the joint includes a bending joint, and
wherein the setting of the rotational angle of the joint to the reference angle includes setting a rotational angle of the bending joint to an angle that allows an operation of folding the object to be rotated coupled to the joint.

7. A manipulator comprising:
a medical instrument having a joint that rotates an object to be rotated;
a driving force transmission that transmits a driving force to the joint;
an actuator that supplies the driving force to the driving force transmission;
a coupling capable of being switched between a driving force relay state where the driving force is relayed and a driving force release state where the driving force is cut off;
a reference angle maintaining mechanism configured to set a rotational angle of the joint to a reference angle that has been predetermined, and maintains the reference angle in a state where the coupling is switched to the driving force release state; and
a controller configured to:
rotate the joint from the reference angle by a predetermined angle in response to the coupling being switched to the driving force relay state, in order to align the joint in an origin orientation different from an orientation at the reference angle, and the actuator rotates to a drive origin as the joint rotates from the reference angle; and
set a rotational position of the actuator based on the rotation of the actuator to the drive origin.

8. The manipulator according to claim 7, wherein the reference angle includes an upper limit and a lower limit in which the rotational angle of the joint can be set.

9. The manipulator according to claim 7,
wherein the controller is further configured to adjust the rotational angle of the joint to the predetermined angle from the reference angle before the controller sets the rotational position of the actuator.

10. The manipulator according to claim 7,
wherein the controller is further configured to set a drive limit from the drive origin when the joint is driven, with respect to the actuator.

11. The manipulator according to claim 7,
wherein the reference angle maintaining mechanism is further configured to apply a biasing force to a rotating body that drives the joint, and maintains the rotational angle of the joint at the reference angle.

12. The manipulator according to claim 11,
wherein the reference angle maintaining mechanism is further configured to apply the biasing force to the joint via the driving force transmission.

13. The manipulator according to claim 7,
wherein the driving force transmission includes a linear driving force transmission member, and
wherein an initial tension application part is further included to apply an initial tension to the driving force transmission member in order to remove loosening of the driving force transmission member in the driving force release state.

14. The manipulator according to claim 7,
wherein the joint includes a bending joint, and
wherein the reference angle maintaining mechanism is further configured to set a reference angle of the bending joint to a rotational angle that becomes a rotational limit for allowing an operation of folding the object to be rotated coupled to the joint.

15. The manipulator according to claim 7, wherein the actuator is a motor.

* * * * *